United States Patent [19]
Nagel et al.

[11] Patent Number: 5,498,549
[45] Date of Patent: Mar. 12, 1996

[54] SENSORS AND METHODS FOR SENSING

[75] Inventors: Colleen C. Nagel, Arden Hills; James G. Bentsen, North St. Paul, both of Minn.; Masao Yafuso, Lake Forest, Calif.; Alan R. Katritzky, Gainesville, Fla.; John L. Dektar, Laguna Hills, Calif.; Cary A. Kipke, Woodbury, Minn.

[73] Assignee: Minnesota Mining and Manufacturing Company, St. Paul, Minn.

[21] Appl. No.: 373,855

[22] Filed: Jan. 18, 1995

Related U.S. Application Data

[60] Division of Ser. No. 137,289, Oct. 14, 1993, Pat. No. 5,409,666, which is a continuation-in-part of Ser. No. 786,189, Oct. 31, 1991, abandoned, and Ser. No. 786,014, Oct. 31, 1991, abandoned, which is a continuation-in-part of Ser. No. 740,790, Aug. 8, 1991, abandoned, and Ser. No. 742,002, Aug. 8, 1991, Pat. No. 5,296,381.

[51] Int. Cl.⁶ .......................... G01N 21/64; G01N 21/77
[52] U.S. Cl. .......................... 436/172; 422/55; 422/58; 422/82.05; 422/82.08; 422/82.11; 436/68; 436/178
[58] Field of Search ............ 436/172, 68, 136, 436/138, 178; 422/82.05, 82.11, 86, 55, 58

[56] References Cited

U.S. PATENT DOCUMENTS

Re. 31,879  5/1985  Lubbers et al. ............... 436/133

(List continued on next page.)

FOREIGN PATENT DOCUMENTS 2009024  8/1990  Canada.
2015415  10/1990  Canada.

(List continued on next page.)

OTHER PUBLICATIONS

"Luminescence Ratio Indicators for Oxygen", Lee et al., *Anal. Chem.*, 1987, 59, 279–283.

(List continued on next page.)

Primary Examiner—James C. Housel
Assistant Examiner—Long V. Le
Attorney, Agent, or Firm—Gary L. Griswold; Walter N. Kirn; F. Andrew Ubel

[57] ABSTRACT

A sensor for measuring the concentration of an analyte in a medium is disclosed. In one embodiment, the sensor comprises a sensing element including a matrix material and, covalently bonded thereto, one or more monomeric indicator components each of which is capable of providing a first emitted signal of a given wavelength in response to being exposed to an excitation signal. The sensing element is capable of providing a second emitted signal having a longer wavelength than the first emitted signal or signals in response to being exposed to the excitation signal, the second emitted signal being provided by an excimer component produced in the sensing element from the monomeric indicator component(s) and being dependent on the concentration of the analyte in the medium to a greater extent than the first emitted signal or signals. In another embodiment, the sensor comprises a sensing element including two or more different monomeric components at least one or which is a monomeric indicator component capable of providing a first emitted signal in response to being exposed to a first excitation signal. The sensing element is capable of providing a second emitted signal in response to being exposed to a second excitation signal. This second emitted signal is provided by an exciplex produced from the monomeric components. This second emitted signal is preferably dependent on the concentration of the analyte in the medium. An excitation assembly is positioned and adapted to provide the excitation signal to the sensing element. A detector assembly is positioned and adapted to detect the second emitted signal. Preferably, a processor assembly is positioned and adapted to analyze the second emitted signal in determining the concentration of the analyte in the medium.

31 Claims, 4 Drawing Sheets

U.S. PATENT DOCUMENTS

| | | | |
|---|---|---|---|
| 3,612,866 | 10/1971 | Stevens . | |
| 3,725,648 | 4/1973 | Schmick et al. | 235/92 C |
| 3,725,658 | 4/1973 | Stanley et al. . | |
| 4,041,932 | 8/1977 | Fostick | 128/2 G |
| 4,194,877 | 3/1980 | Peterson . | |
| 4,468,229 | 8/1984 | Su | 8/507 |
| 4,548,907 | 10/1985 | Seitz et al. | 436/163 |
| 4,557,900 | 12/1985 | Heitzmann | 422/55 |
| 4,640,820 | 2/1987 | Cooper | 422/68 |
| 4,657,736 | 4/1987 | Marsoner et al. | 422/56 |
| 4,712,865 | 12/1987 | Hsu et al. | 8/523 |
| 4,714,770 | 12/1987 | Hsu et al. | 8/523 |
| 4,746,751 | 5/1988 | Oviatt, Jr. et al. | 8/506 |
| 4,775,514 | 10/1988 | Barnikol et al. | 422/55 |
| 4,798,738 | 1/1989 | Yafuso et al. | 427/2 |
| 4,803,049 | 2/1989 | Hirschfeld et al. | 58/170 |
| 4,824,789 | 4/1989 | Yafuso et al. | 436/68 |
| 4,830,013 | 5/1989 | Maxwell | 128/637 |
| 4,840,485 | 6/1989 | Gratton | 356/317 |
| 4,849,172 | 7/1989 | Yafuso et al. | 422/55 |
| 4,867,919 | 9/1989 | Yafuso et al. | 264/1.5 |
| 4,900,933 | 2/1990 | Nestor et al. | 250/458.1 |
| 4,916,160 | 4/1990 | Boardman et al. | 522/27 |
| 4,929,561 | 5/1990 | Hirschfeld | 436/116 |
| 4,989,606 | 2/1991 | Gehrich et al. | 128/637 |
| 5,015,715 | 5/1991 | Divers et al. | 528/15 |
| 5,019,350 | 5/1991 | Rhum et al. | 422/82.07 |
| 5,030,420 | 7/1991 | Bacon et al. | 422/82.07 |
| 5,037,615 | 8/1991 | Kane | 422/82.08 |
| 5,094,958 | 3/1992 | Klainer et al. | 436/172 |

FOREIGN PATENT DOCUMENTS

| | | |
|---|---|---|
| 0109959 | 5/1984 | European Pat. Off. . |
| 0263693 | 4/1988 | European Pat. Off. . |
| 0283206 | 9/1988 | European Pat. Off. . |
| 0368481 | 5/1990 | European Pat. Off. . |
| 0301026 | 8/1990 | European Pat. Off. . |
| 0381026 | 8/1990 | European Pat. Off. . |
| 0363219 | 11/1990 | European Pat. Off. . |
| 0413114 | 2/1991 | European Pat. Off. . |
| 0413499 | 2/1991 | European Pat. Off. . |
| 0442276 | 8/1991 | European Pat. Off. . |
| 106086 | 5/1974 | Germany . |
| 2132348 | 7/1984 | United Kingdom . |
| WO8805533 | 7/1988 | WIPO . |

OTHER PUBLICATIONS

"Host–Guest Sensory Systems for Detecting Organic Compounds by Pyrene Excimer Fluorescence", A. Ueno, *Anal. Chem.*, 1990, 2461–2466.

"Unusually Efficient Quenching of the Fluorescence of an Energy Transfer–Based Optical Sensor for Oxygen", Sharma and Wolfbeis, *Analytica Chimica Acta.*, 212 (1988) 261–265.

Berlman et al., "On the fluorescence spectrum and decay time of naphthalene", Mol. Phys. 5, 313 (1962).

Yanari et al., "Fluorescence of Styrene Homopolymers and Copolymers", Nature, 1963, vol. 200.

Fumio Hirayama, Intramolecular Excimer Formation. I. Diphenyl and Tripheny Alkanes, The Journal of Chemical Physics, vol. 42, No. 9, 1965.

Kroneis et al., A Fluorescence–Based Sterilizable Oxygen Probe for Use in Bioreactors, Sensors and Actuators, 4 (1983) 587–592.

Rehm and Weller, Bindungszustand und Fluoreszenzspektren von Hetero–Excimeren, Patentschrift für Physikalische Chemie Neue Folge, Bd. 69, S. 183–200 (1970).

Hui et al., An accurate, Low–Cost, Easily–Manufacturable Oxygen Sensor, SPIE vol. 1172 Chemical, Biochemical, and Environmental Sensors (1989) pp. 233–238.

Barton et al., Organosilicon Chemistry, 1990 American Chemical Society.

Wolfbeis, Otto, Oxygen Sensors, Fiber Optic Chemical Sensors and Biosensors, vol. II, 19–53, 1991.

Wolfbeis, Otto, Appendix: A Selection of Relevant Patents, vol. I, 17–21, 1991, Fiber Optic Chemical Sensors and Biosensors.

Wolfbeis, Otto, VIII. Internal Referencing, and IX Rejection of Interfering Light, Fibjer Optic Chemical Sensors & Biosensors, vol. I, 102–110, 199.

Lakowicz, Joseph R., Spectral Characteristics of Systems Which Undergo a Reversible Two–State Reaction, Principles of Fluorescence Spectroscopy, 1983, 383–429.

Weller, "Singlet–And Triplet–State Exciplexes", The Exciplex, Academic Press Inc., New York (1975) pp. 23–38.

J. Lakowicz, "Measurement of Fluorescence Liftimes", Principles of Fluorescence Spectroscopy, Plenum Press (1986).

W. Ware, Oxygen Quenching of Fluorescence in Solution: An Experimental Study of the Diffusion Process, 1962, vol. 66, 455–458.

Cherkasov et al., Excited Dimers (Excimers) of Anthracene Derivatives and Concentration Quenching of Fluorescence, Akad Nauk USSR Bull Phys. Science, 29, 1288–1299 (1965).

Veselova et al., Luminescent properties of exciplexes of phthalimide derivatives with tetramethylidiaminodiphenylmethane, Opt. Spectrosc., vol. 42, No. 1, 1977, 39–43.

Lakowicz et al., Theory of Phase–Modulation Fluorescence Spectroscopy For Excited–State Processes, Biophysical Chem., 16 (1982) 99–115.

Lakowicz et al., Analysis of Excite–State Processes by Phase–Modulation Fluorescence Spectroscopy, Biophysical Chem 16 (1982) 117–132.

Bright, Frank V., A New Fiber–Optic–Based Multifrequency Phase–Modulation Fluorometer, Applied Spectroscopy, vol. 42, No. 8, 1988, 1531–153.

Lakowicz et al. Detection of the Reversibility of an Excited–State Reaction by Phase–Modulation Fluorometry, Chemical Physics Letter, vol. 92, No. 2, 1982, 117–121.

Sharma et al., Fiberoptic Oxygen Sensor Based on Fluorescence Quenching and Energy Transfer, Applied Spectroscopy, vol. 42, No. 6, 1988.

Birks, Photophysics of Aromatic Molecules, 1970.

Lippitsch et al., Fibre–Optic Oxygen Sensor with the Fluorescence–Decay Time as the Information Carrier, Anal. Chimica Acta, 205(1988) 1–6.

Merlo et al., Development of a Fluorescence–Based Fiber Optic Sensor for Rapid Detection of General Anesthetics and Other Lipid–Soluble Chemical, Ultrasonic and Optical Sensors.

"Exciplexes and Electron Transfer Reactions", Mattes et al., Science, vol. 226, No. 4677, pp. 917–921 (1984).

"Fiber Optic Fluorosensor for Sulfor Dioxide Based on Energy Transfer and Exciplex Quenching", SPIE, vol. 990, pp. 116–120 (1988), Sharma et al.

SENSORS AND METHODS FOR SENSING

RELATED APPLICATIONS

This application s a division of application Ser. No. 08/137,289 filed Oct. 14, 1993 U.S. Pat. No. 5,409,666 which is a continuation-in-part of application Ser. No. 07/786,189, filed Oct. 31, 1991 (abandoned) and application Ser. No. 07/786,014 filed Oct. 31, 1991, (abandoned) which is a continuation-in-part of application Ser. No. 07/740,790, filed Aug. 8, 1991 (abandoned) and a continuation-in-part of application Ser. No. 7/742,002, filed Aug. 8, 1991 (U.S. Pat. No. 5,296,381) which are herein incorporated by reference.

FIELD OF THE INVENTION

The present invention relates generally to sensors for measuring the concentration of an analyte of interest in a medium. In particular, the present invention includes a sensor for the monitoring of blood gas (e.g., oxygen, ionized hydrogen and carbon dioxide) concentrations.

BACKGROUND OF THE INVENTION

The present invention relates to sensing or determining the concentration of an analyte of interest in a medium. More particularly, the invention relates to sensor apparatus or systems and methods for sensing the concentration of an analyte of interest, for example, oxygen, in a medium, for example, blood. It is sometimes necessary or desirable for a physician to determine the concentration of certain gases, e.g., oxygen and carbon dioxide, in blood. This can be accomplished utilizing an optical sensor which contains an optical indicator responsive to the component or analyte of interest. The optical sensor is exposed to the blood, and excitation light is provided to the sensor so that the optical indicator can provide an optical signal indicative of a characteristic of the analyte of interest. For example, the optical indicator may fluoresce and provide a fluorescent optical signal as described in Lubbers et at. U.S. Pat. Re No. 31,897 or it may function on the principles of light absorbance as described, for example, in Fostick U.S. Pat. No. 4,041,932.

The use of optical fibers has been suggested as part of such sensor systems. The optical indicator is placed at the end of an optical fiber which is placed in the medium to be analyzed. This approach has many advantages, particularly when it is desired to determine a concentration of analyte in a medium inside a patient's body. The optical fiber/indicator combination can be made sufficiently small in size to easily enter and remain in the cardiovascular system of the patient. Consistent and accurate concentration determinations are obtained. Luminescence measurement analysis for monitoring concentrations of analytes is well known in the art. Generally, a calibration curve of light intensity (or a function of intensity) vs. concentration of the analyte is made. This method may involve a determination of absolute light intensifies of both excitation and emission. In phase modulation detection methods, luminescent indicators are excited by an intensity modulated excitation source and the phase shift between the excitation and emission signals can be used to determine an analyte dependent luminescence lifetime.

One problem which may exist in such systems is the wavelength proximity between the excitation signal (light) and the emission signal (light) of the indicator. In many cases, the excitation signal and emission signal each have relatively similar wavelengths. This can result in misinterpreting the emission signal, which misinterpretation results in an inaccurate determination of the analyte concentration. It would be advantageous to provide a sensing system in which the wavelengths of the excitation and emission signals are substantially different.

It would be advantageous to provide a sensor system in which the lifetime, and preferably both the lifetime and intensity, of the differentiated emitted signal are sensitive to analyte concentration in a medium. Emissions, for example, fluorescent emissions, which are sensitive or dependent in terms of both lifetime and intensity to analyte concentration are said to be dynamically quenchable by the analyte.

While substantial differentiation of the excitation and emission signals can be achieved using phosphorescent organic indicators, dye stability is often a problem. Indeed, Stanley et al. U.S. Pat. No. 3,725,648, explicitly excludes phosphorescent molecules as potential sensor materials because of the stability problems. Some phosphorescent platinum group inorganic complexes and phosphorescent lanthanide complexes have shown suitable stability but are quite expensive and may generate significant amounts of highly reactive singlet oxygen upon irradiation in the presence of oxygen. It would be advantageous to provide a sensing system in which substantial differentiation of excitation and emission signals is achieved using stable dyes, e.g., with reduced, or no, generation of reactive species, such as singlet oxygen.

Substantial differentiation of the excitation and emission signals can be achieved with an excited singlet state by using energy transfer from an analyte responsive first dye to an analyte insensitive second dye (Barnet et at. European Pat. No. 381,026). Energy transfer is a collisionless process that occurs through space and requires substantial optical overlap between the characteristic emission of the first dye and the characteristic absorption of the second dye. The first dye absorbs light at a characteristic excitation wavelength and its excited state energy is transferred to the second dye. In this way, the second dye can emit at its own characteristic emission wavelength in response to excitation of the first dye. An analyte that quenches the emission from the first dye also quenches the energy transfer to the second dye. Therefore, the emission of the second dye is indirectly influenced by analyte and a substantial shift between excitation and emission wavelengths is achieved. For energy transfer to occur several requirements must be met. First, two different indicators are required and both indicators must fluoresce. Second, there must be overlap between the characteristic emission of the first dye and the characteristic absorption of the second dye. Third, to prevent analyte insensitive emission, the second dye must not absorb light at the excitation wavelength of the first dye. In addition to the above requirements, excited state collisional interactions between dye molecules can quench energy transfer. Barner et at. discloses methods to prevent unwanted collisional interactions.

Unwanted collisional interactions are further discussed by Sharma et at. in "Unusually Efficient Quenching of the Fluorescence of An Energy Transfer-Based Optical Sensor for Oxygen", Analytica Chimica Acta, 212 (1988) 261–265. They disclose a two fluorophor energy transfer based sensor consisting of pyrene (their analyte responsive first dye) and perylene (their analyte insensitive second dye) both dispersed in silicone rubber. In response to excitation of the pyrene using a 320 nm excitation signal a fluorescent signal (characteristic of the emission wavelength of perylene) is observed at 474 nm. Sharma et at. concluded that the 474 nm emitted signal resulted in part from perylene emission and in part from a collisional interaction between the pyrene and perylene thereby forming an emissive excited state complex which they called an exciplex. The interference of exciplex emission with perylene emission is presently believed to be undesirable. No covalent bonding of pyrene and perylene to the silicone rubber is disclosed so that there is not teaching or suggestion as to how such covalent bonding affects the system. It would clearly be advantageous to employ an emitted signal for analyte concentration determination that is substantially removed or resolved from other emissions in the system. Furthermore, it would be advantageous to obtain this signal by some means other than energy transfer.

Pyrene excimer emission has been successfully employed in solutions for the detection of organic compounds (Ueno et at., Anal. Chem., 1990, 62, 2461–66) and anesthetics (Merlo et at., IEEE Engineering in Medicine & Biology, 11th Annual International Conference Proceedings, 1989), with excimer fluorescence serving as a reporter of the aggregation of cyclodextrins or of a change in the local viscosity, respectively. These sensing mechanisms work on the premise of an analyte suppressing or enhancing the efficiency for population of an emissive excited state. These systems are not disclosed as being usable in solid sensing elements. An additional problem with such systems is that they are incompatible with phase modulated detection methods, since the lifetime of the emissive state is substantially independent of analyte concentration.

Fiber-optic based sensors are very useful, for example, in medical applications. One problem which may exist with such systems is related to the inherent flexibility of optical fibers. These flexible fibers have a tendency to bend which, in turn, distorts the signals being transmitted by the fibers to the signal processor. Signal distortion caused by fiber bends or other sensor system problems result in inaccurate concentration determinations. It would be advantageous to provide a sensor and concentration determination method which provide accurate concentration data in spite of such distortions.

Seitz et al. (U.S. Pat. No. 4,548,907) discloses a fluorescence-based optical sensor which includes a fluorophor having an acid form and a base form. Specifically, the relative amounts of the acid form and base form vary depending on the pH of the medium. The fluorophor is excited at two different wavelengths, one for the acid form and one for the base form, and fluorescence signals at a single wavelength are detected. By ratioing the fluorescence signals obtained at the two different excitation wavelengths, the pH of the medium can be determined independent of amplitude distortions which affect both signals equally. This sensor has the advantage of using a single fluorophor. However, the sensor of this patent is limited in that only those analytes which influence the ratio of acid form to base form of the fluorophor can be monitored. Again, the emission lifetimes are substantially independent of analyte concentration. Also, no other multiple state optical indicators are taught or suggested.

Lee, et at. in "Luminescence Ratio Indicators for Oxygen", Anal. Chem., 59, p. 279–283, 1987, report on work the goal of which was to develop a single reagent that would show two luminescence bands, a shorter wavelength "analytical" band subject to quenching by oxygen and a longer wavelength "reference" band independent of oxygen levels. Specifically, the work was to formulate a system showing both shorter wavelength oxygen-sensitive pyrene monomer emission and longer wavelength oxygen-insensitive pyrene dimer emission. This work did not succeed in finding a ratio-based indicator system to measure oxygen in aqueous systems. Further, as noted above, using a shorter wavelength oxygen sensitive emission can result in oxygen concentration determination inaccuracies because of possible overlapping between this short wavelength emission and the excitation signal.

Canadian Patent Application 2,015,415 (Divers et at.) discloses an oxygen sensor including a single species of indicator selected from perylene derivatives dispersed or immobilized in a crosslinked polydimethylsiloxane matrix which gives a shorter wavelength oxygen sensitive emission and a longer wavelength oxygen insensitive emission and, thus, can be used as both the indicator and the reference element. Using shorter wavelength oxygen sensitive emission can result in inaccuracies because of overlap with the excitation signal, as described above. Also, there is no teaching or suggestion that the shorter and longer wavelength emissions are the result of different forms of the indicator. To the contrary, the document implies that a single indicator species provides an oxygen-sensitive emission region and a different oxygen-insensitive emission region.

European Patent Publication 0 363 219 (Barnes) discloses an oxygen sensing apparatus using Europium or Erythrosin-B as phosphors which are excited with a monochromatic light that is sine wave modulated in the kHz regime. The emitted light of a different wavelength is also sine wave modulated, with the phase difference between the two sine waves being a measure of the quenching effect of oxygen and, thus, a measure of the partial pressure of oxygen. This publication does not disclose the use of any other indicators, for example, fluorescent indicators. Modulation in the kHz region cannot be extended to shorter lived fluorescent indicators because the phase offsets introduced by transmission of the excitation and emission signals, e.g., through an optical fiber, become significant. Also, there is no teaching or suggestion that the phosphors used produce different emitting forms. Further, as noted above, the use of phosphorescent indicators can result in other problems.

SUMMARY OF THE INVENTION

The present invention provides sensors and methods for sensing the concentration, for example, partial pressure, of a component or analyte of interest, such as oxygen, in a medium, for example, an aqueous-based medium, such as blood. The present systems function to give accurate, reliable and reproducible concentration determinations. In addition, such determinations can be provided in spite of signal transmission problems, such as, bent optical fibers, and other operational difficulties which may affect the quality of the signals being transmitted. Further, efficient utilization of the indicator component or components is achieved often resulting in sensors having reduced indicator component loadings. Moreover, these advantageous results are achieved using sensors, equipment and techniques which are relatively simple, easily operated and conveniently executed.

In one broad aspect, the present sensors comprise a sensing element, an excitation assembly and a detector assembly, wherein the sensing element includes one or more, preferably one or two, monomeric indicator components, preferably located in, more preferably covalently bonded to, a matrix material, preferably a solid matrix material. Each of these monomeric indicator components is capable of providing a first emitted signal of a given wavelength in response to being exposed to a first excitation signal. Further, this sensing element is capable of providing a second emitted signal (due to emission by the excited site complex), preferably having a longer wavelength than the first emitted signal or signals, in response to being exposed to a second excitation signal.

In another broad aspect, the present sensors comprise a sensing element, an excitation assembly and a detector assembly, wherein the sensing element includes two or more different monomeric components at least one of which is a monomeric indicator component, each of which monomeric components is preferably located in, more preferably covalently bonded to, a matrix material, preferably a solid matrix material. The monomeric indicator component is capable of providing a first emitted signal of a given wavelength in response to being exposed to a first excitation signal. This sensing element is capable of providing a second emitted signal (due to emission by the excited state complex), preferably having a longer wavelength than the first emitted signal, in response to being exposed to the second excitation signal.

Preferably, the first excitation signal or signals and the second excitation signal are the same signal. The second emitted signal is provided by an excimer component produced in the sensing element from the monomeric indicator component(s) or by an exciplex component produced, for example, in the sensing element, from the monomeric components and is preferably more dependent on, i.e., varies in response to changes in, the concentration of the analyte in the medium to which the sensing element is exposed than the first emitted signal or signals. That is, for example, the excited state complex derived second emitted signal is dynamically quenched or subject to being dynamically quenched by the analyte to a greater extent than the first emitted signal or signals. Excited state complex emissions which are dynamically quenchable are preferred because, for example, they are useful in both intensity-based and "phase-modulation" detection sensing systems.

The excitation assembly is positioned and adapted to provide one or more excitation signals to the sensing element. Such excitation signals preferably each have a wavelength which is shorter than the first emitted signal or signals. The first and second excitation signals may each have substantially the same wavelength.

The detector assembly is positioned and adapted to detect either the second emitted signal from the sensing element, or the first emitted signal or signals and the second emitted signal from the sensing element.

The processor assembly is preferably positioned and adapted to process or analyze either the second emitted signal in determining the concentration of the analyte in the medium, or the first emitted signal or signals and the second emitted signal in determining the concentration of the analyte in the medium.

Using the excited state complex provided second emitted signal as at least part of the basis for the analyte concentration determination provides substantial benefits. This second emitted signal is different and distinct from the first emitted signal or signals provided by the monomeric indicator component(s). This second emitted signal has a relatively long wavelength and, thus, is further shifted away (red-shifted) from the excitation signal or signals than is the first emitted signal or signals. Thus, there is reduced risk of misinterpreting the second emitted signal (for example, because of interference from the excitation signal or signals) than of misinterpreting the relatively shorter wavelength first emitted signal or signals.

A particularly useful embodiment (known as "phase-modulation detection") involves a sensing element which provides an intensity modulated, preferably a sine wave modulated, second emitted signal in response to being exposed to an intensity modulated, preferably a sine wave modulated, second excitation signal. This modulated second emitted signal is provided by an excited state complex produced in the sensing element. The processor assembly is positioned and adapted to analyze the modulated second emitted signal and the modulated second excitation signal in determining the concentration of the analyte in the medium.

As used herein, the term "relative demodulation" refers to the demodulation factor for the modulated emitted signal with respect to the modulated excitation signal which results in the modulated emitted signal. The use of the excited state complex provided modulated second emitted signal as a basis for analyte concentration determinations provides substantial benefits, for example, in terms of very good analyte concentration accuracy determination. The modulated signals referred to herein may be modulated in the MHz range, as opposed to being limited to the kHz range as disclosed in European Patent Publication No. 0 363 219 noted above. The use of the extent of the phase shift and/or the magnitude of relative demodulation, as described herein, at a variety of modulation frequencies can be used to determine analyte concentration, and is included within the scope of the present invention.

In practice, phase-modulation detection can be implemented in a number of different modes, all of which generate a concentration dependent parameter which varies as a function of the analyte concentration. These phase-modulation detection modes include:

1. Phase shift vs. analyte concentration at constant modulation frequency;
2. Demodulation factor vs. analyte concentration at constant modulation frequency;
3. Modulation frequency vs. analyte concentration at constant phase shift;
4. Modulation frequency vs. analyte concentration at constant demodulation factor; and
5. Multifrequency phase and/or modulation vs. analyte concentration.

In one embodiment, the processor assembly is adapted to determine the intensity ratio of the second emitted signal to the first emitted signal or one of the first emitted signals (or vice versa). Such a signal ratio is itself preferably dependent on the concentration of the analyte in the medium. The first emitted signal or signals may also be dependent on the concentration of the analyte in the medium.

In another embodiment, the first emitted signal or signals and the second emitted signal are intensity modulated (e.g., in response to exposing the monomeric component(s) to an intensity modulated excitation signal or signals), and the processor assembly is adapted to determine the extent of the phase shift and/or the magnitude of relative demodulation between the modulated second excitation signal and the modulated second emitted signal. Preferably, the signals are sine wave modulated. The extent of this shift and/or magnitude of relative demodulation is dependent on the concentration of the analyte in the medium.

In another embodiment, the first emitted signal or signals and the second emitted signal are intensity modulated (e.g., in response to exposing the monomeric component(s) to an intensity modulated excitation signal or signals), and the processor assembly is adapted to determine the extent of the phase shift between the modulated first emitted signal(s) and the modulated second emitted signal. Preferably, the signals are sine wave modulated. The extent of this shift is dependent on the concentration of the analyte in the medium.

In another embodiment, the first emitted signal or signals and the second emitted signal are intensity modulated (e.g., in response to exposing the monomeric component(s) to an intensity modulated excitation signal or signals), and the processor assembly is adapted to determine the extent of phase shift between the combined modulated first and second emitted signals and the first excitation signal or signals. The extent of this shift is dependent on the concentration of the analyte in the medium.

In another embodiment, the first emitted signal or signals and the second emitted signal are intensity modulated (e.g., in response to exposing the monomeric component(s) to an intensity modulated excitation signal or signals), and the processor assembly is adapted to determine the ratio of demodulation factors of the modulated first emitted signal (or one of the modulated first emitted signals) and the modulated second emitted signal. The extent of this ratio is dependent on the concentration of the analyte in the medium.

In another embodiment, the first emitted signal or signals and the second emitted signal are intensity modulated (e.g., in response to exposing the monomeric component(s) to an intensity modulated excitation signal or signals), and the processor assembly is adapted to determine the magnitude of relative demodulation between the combined modulated first and second emitted signals and the combined modulated first and second excitation signals. The extent of this magnitude of relative demodulation is dependent on the concentration of the analyte in the medium.

In another embodiment, the modulated first and second emitted signals are monitored and the intensity modulated excitation signal is adjusted in frequency so as to maintain a fixed phase difference between the modulated first and second emitted signals. For example, by adjusting the excitation frequency the phase shift is held to a fixed value. The excitation frequency necessary to maintain a fixed phase shift between the modulated first and second emitted signals is dependent on the concentration of the analyte in the medium.

In another embodiment (further described in the copending and commonly assigned U.S. Patent Application, filed on even date herewith, entitled "Emission Quenching Sensors", Ser. No. 08/136,967, which is herein incorporated by reference) the sensing instrument includes a sensing element configured for exposure to an analyte and including at least a first fluorescable monomeric indicator component for which the excited state complex emission is characterized by a bimolecular quenching rate constant $k_q$ for the quencher (e.g., the analyte of interest), one or more fluorescence lifetimes $\tau_o$ above a lowest lifetime $\tau_{oL}$ for the impulse response function of the excited state complex, and capable of emitting analyte concentration dependent signals having a concentration dependent parameter which varies as a function of analyte concentration when exposed to an excitation signal in the presence of analyte. An excitation system coupled to the sensing element provides the excitation signal at one or more radial frequencies $\omega$. A detector coupled to the sensing element detects the analyte concentration dependent signals and provides detected signals. A processor including memory for storing information characterizing a calibration relationship between analyte concentration and the concentration dependent parameter is coupled to the detector. The processor univariantly processes the detected signals to derive the concentration dependent parameter, and provides output signals representative of analyte concentration as a function of the derived concentration dependent parameter and the stored information. The sensing element and/or excitation system are configured to enable the instrument to operate sufficiently within the condition $[(k_q[Q])^2+\omega^2]\tau_o^2 \gg 1+2k_q\tau_o[Q]$ such that a slope of the relationship between the concentration dependent parameter and analyte concentration is independent of $\tau_o$ variability for all analyte concentrations within the operating range and for all lifetimes $\tau_o$ greater than $\tau_{oL}$. When configured in this manner the sensor is independent of $\tau_o$ variability. The sensor can therefore be recalibrated by modifying the stored calibration information characterizing the intercept, but not the slope, of the relationship in response to sensing element exposure to one calibration analyte of a known concentration. In one configuration the sensing instrument includes an excitation system for providing the excitation signal at high frequencies enabling the instrument to operate within the condition $\omega\tau_o > 10$ for all analyte concentrations within the operating range and for all lifetimes $\tau_o$ greater than $\tau_{oL}$. In another configuration the sensing element is characterized by a sufficiently large solubility and/or diffusivity to enable the instrument to operate under the condition $k_q\tau_o[Q] > 20$ for all analyte concentrations within the operating range and for all lifetimes $\tau_o$ greater than $\tau_{oL}$. In another configuration of the sensing instrument the sensing element and/or excitation system are configured to enable the instrument to operate sufficiently within the condition $[(k_q[Q])^2+\omega^2]\tau_o^2 \gg 1+2k_q\tau_o[Q]$ such that both slope and intercept of the relationship between the concentration dependent parameter and analyte concentration is independent of $\tau_o$ variability for all analyte concentrations within the operating range and for all lifetimes $\tau_o$ greater than $\tau_{oL}$. Recalibration of the sensing instrument is therefore unnecessary.

Modes 1 through 4 can also be practiced with or combined with multiharmonic frequency methods. Sensing instruments such as these can be characterized as "multivariant" systems since the excitation signal contains a broad range of frequencies and the emission signal exhibits a similar frequency content. Multivariant systems of this type inquire deconvolution of the emission signal, e.g., by Fourier analysis software. The frequency domain information derived by this multivariant processing approach is further processed to obtain values for lifetimes or Stern-Volmer slopes, and these values are in turn translated into analyte concentration.

Using the aforementioned signal ratio or both the modulated first emitted signal or signals and the modulated second emitted signal in determining the analyte concentration reduces, or even substantially eliminates, the detrimental effect on the accuracy of the concentration determination caused by, for example, distortion in the signals, for example, as the result of bent optical fibers. One particular advantage of excited state complex forming systems having one monomeric indicator component and one monomeric non-indicator component over internally referenced systems containing a separate second indicator dye is that the analyte sensitive emission and the reference emission can be well resolved from one another using a single excitation wavelength. Furthermore, the intensity ratio, or the phase difference or the demodulation factor ratio methods can provide linear Stern-Volmer calibration slopes substantially independent of indicator component degradation.

The use of modulated signals, as described herein, is intensity independent. That is, the use of an analyte sensitive extent of shift in modulated signals is applicable regardless of the intensity of the signals used. The use of such modulated signals provides for very reliable and reproducible analyte concentration determinations.

In yet another broad aspect, the invention involves methods for sensing the concentration, for example, partial pressure, of an analyte, for example, oxygen or other normally gaseous component, in a medium, such as blood or other aqueous, for example, liquid aqueous, medium. These methods comprise: exposing a sensing element, as described herein, to the medium; causing the sensing element to provide a second excited state complex provided emitted signal, or first monomeric indicator component provided emitted signal or signals and a second excited state complex provided emitted signal, as described herein; and analyzing the second emitted signal or at least one of the first emitted signals and the second emitted signal in determining the concentration of analyte in the medium. The excitation signal or signals may also be analyzed in these methods.

A still further broad aspect of the present invention is the provision of compositions, for example sensing elements, useful for measuring the concentration of an analyte in a medium.

In one embodiment, the compositions comprise a solid matrix material which is permeable to the analyte in the medium, and an effective amount of an "indicator component" in enforced association (e.g., a tethered bichromophoric indicator component) in, for example, within and/or on, preferably within, the matrix material. The indicator component includes a first monomeric indicator component capable of providing a first emitted signal of a first wavelength in response to being exposed to a first excitation signal, and a second related monomeric indicator component capable of providing another first emitted signal of a second given wavelength in response to being exposed to a second excitation signal. The first monomeric indicator component is preferably covalently bonded to the second monomeric indicator component, preferably by a linkage which facilitates the appropriate interaction between the first and second monomeric indicator components. The composition is capable of providing a second emitted signal in response to being exposed to a third excitation signal. Preferably the third excitation signal is the same as the first and/or second excitation signals. This second emitted signal is provided by an excimer component produced from the first monomeric indicator component and the second monomeric indicator component. The second emitted signal is dependent on the concentration of the analyte in the medium. This second emitted signal is preferably dynamically quenchable by the analyte in the medium.

One or more of the first emitted signal(s) may also be dependent on the concentration of the analyte in the medium. Preferably, the second emitted signal is dependent on the concentration of the analyte in the medium to a greater extent than are the first emitted signal(s). To control the separation distance between the monomeric indicator components, the indicator component in enforced association is preferably covalently bonded to the solid matrix material, if at all, through a single covalent linkage. In a particularly useful embodiment, the solid matrix material is a silicone-based polymic and the first monomeric indicator component and second monomeric indicator component are preferably selected from polynuclear aromatic species and mixtures thereof.

A particular example of such indicator components are those systems in which two similar fluorescent monomeric indicator components are covalently tethered to each other in such a manner to facilitate the production of the desired excimer component. In one particularly useful embodiment, the number of atoms, for example, carbon atoms, in the chain covalently linking (or "tethering") the first and second species together is in the range of about 1 to about 20, more preferably about 2 to about 7. The tethered indicator component may be attached to the matrix by way of a covalent bond to either monomeric indicator component or to the chain. If desired the chain may have more than one functional groups attached thereto to facilitate covalent bonding to the matrix or to crosslink the matrix material. In one particularly useful embodiment, the monomeric components are covalently linked or bonded together other than through the matrix material.

Employing excited state complex provided second emitted signals which are provided by indicator components which are in enforced association results in increased indicator utilization efficiency. That is, the formation of the excited state complex is advantageously kinetically favored so that relatively less monomeric indicator component or components are needed to form the same amount of excited state complex. Thus, the amount of monomeric component(s) can be reduced and/or even the size of the sensor can be reduced. The use of the excited state complex provided second emitted signal results in accurate, reliable, reproducible and efficient analyte concentration determinations.

In another embodiment, the compositions comprise effective amounts of an indicator component comprising two or more monomeric components, which are preferably covalently linked or bonded together, at least one of which is a monomeric indicator component. The compositions may include a matrix material, preferably a solid matrix .material, which is permeable to the analyte in the medium. The monomeric components may be in, for example, within and/or on, preferably within, the matrix material. The monomeric indicator component is capable of providing a first emitted signal in response to being exposed to a first excitation signal. The covalent bending between the monomeric components is preferably by a linkage which facilitates the appropriate exciplex component-forming interaction between these monomeric components. The composition is capable of providing a second emitted signal in response to being exposed to the second excitation signal. This second emitted signal is provided by an exciplex component produced from the monomeric components. The second emitted signal is preferably dependent on the concentration of the analyte in the medium. This second emitted signal is preferably dynamically quenchable by the analyte in the medium. A particular example of such composition involves those systems in which the monomeric components are covalently tethered to each other in such a manner to facilitate the production of the desired exciplex component. In one particularly useful embodiment, the number of atoms, for example, carbon atoms, in the chain covalently linking the monomeric components together is in the range of about 1 to about 20, more preferably about 2 to about 7.

The first emitted signal of either of the above embodiments may also be dependent on the concentration of the analyte in the medium. Preferably, the excited state complex provided emitted signal (i.e., the second emitted signal) is dependent on the concentration of the analyte in the medium to a greater extent than is the first emitted signal. The monomeric components are preferably covalently bonded to the solid matrix material. The tethered indicator component may be attached to the matrix by way of a covalent bond to either monomeric component or to the chain. If desired the chain may have more than one functional groups attached thereto to facilitate covalent bonding to the matrix or to crosslink the matrix material. In a particularly useful embodiment, the solid matrix material is a silicone-based polymer.

DETAILED DESCRIPTION

Figure 1:
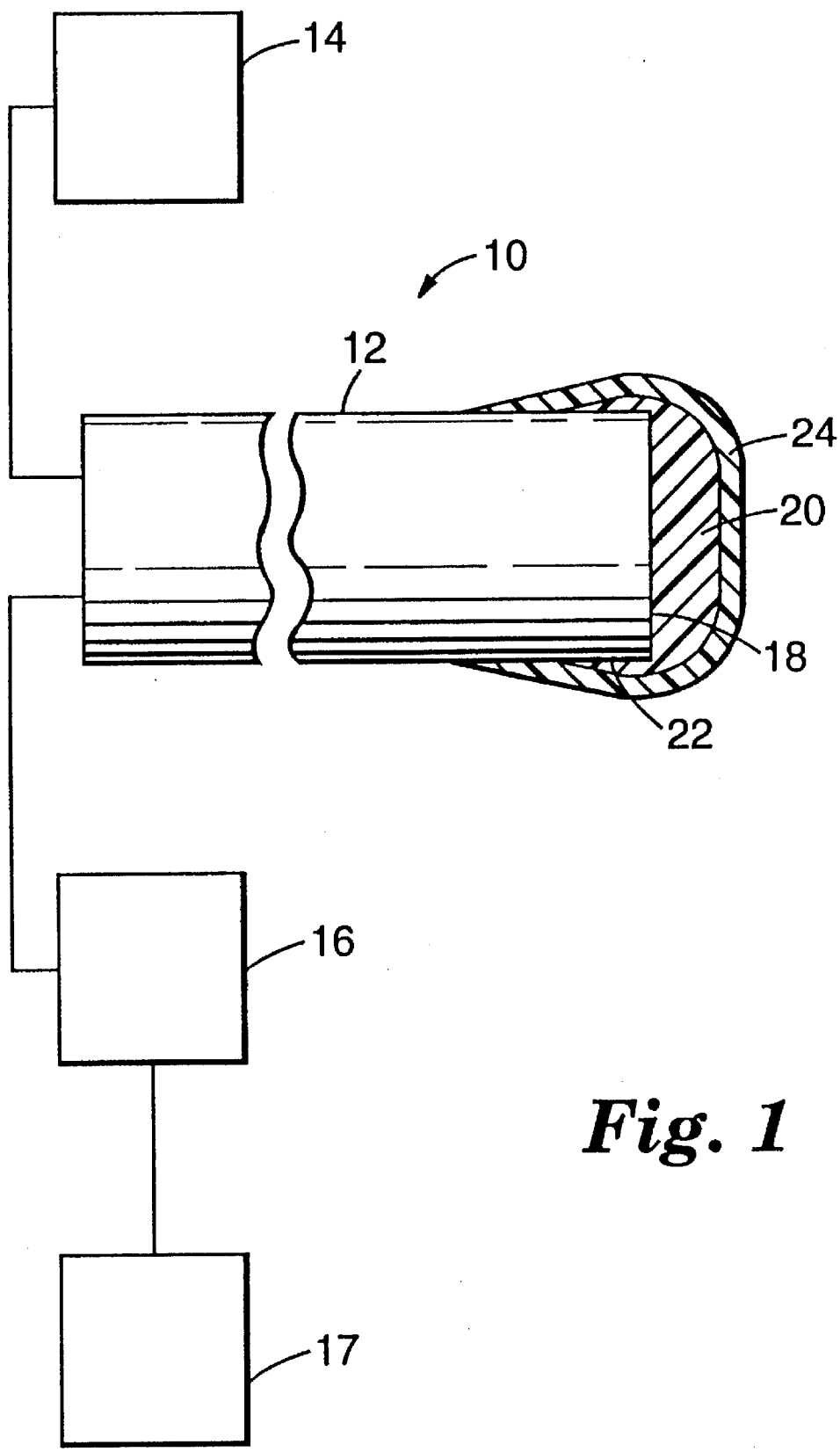
FIG. 1 is a schematic illustration of one embodiment of the sensor apparatus according to the present invention.

As based herein, the term "monomeric component" refers to a species which may or may not itself provide a signal, such as an optically detectable signal, in response to being exposed to an excitation signal, such as an excitation light signal, and which is capable of participating in the formation of an excited state complex.

As used herein, the term "monomeric indicator component" refers to a monomeric component which provides a signal, preferably an optically detectable signal, in response to being exposed to an excitation signal, preferably an excitation light signal. A "fluorescent fluoresable monomeric indicator component" is a monomeric indicator component which provides a fluorescence signal in response to being exposed to an excitation signal.

As used herein, the term "monomeric non-indicator component" refers to a monomeric component which is itself incapable of providing an effective signal, such as an optically detectable signal, in response to being exposed to an excitation signal, such as the first excitation signal employed to excite the monomeric indicator component or the first emitted signal produced by the monomeric indicator component in response to its being exposed to the first excitation signal.

As used herein, the term "indicator component" refers to the combination of two or more monomeric components (at least one of which is a monomeric indicator component) in enforced association. By "enforced association" it is meant that the monomeric component(s) are positioned or oriented in physical and/or molecular enforcement to promote or facilitate the formation and/or maintenance of a channel or path for excited state complex formation which (a) is kinetically dominant relative to free diffusion, and/or (b) is kinetically competitive with the decay of the excited state complex in the absence of the analyte. A "tethered indicator component" is an indicator component wherein two or more monomeric components (at least one of which is a monomeric indicator component) are covalently bonded to each other.

As used herein, the term "excimer component" refers to an excited state complex between two monomeric indicator components, preferably fluorescent monomeric indicator components, which have the same indicator structure and which preferably fluoresces thereby providing a "second emitted signal". Isomers and tautomers of the same monomeric indicator components are included.

As used herein, the term "exciplex component" refers to an excited state complex between two different monomeric components at least one of which is a monomeric indicator component and which preferably fluoresces thereby providing a "second emitted signal". Preferred exciplex components comprise an excited state complex between two different monomeric components wherein one of said components comprises a monomeric indicator component and the other of said components comprises a monomeric non-indicator component.

When fluorescence intensity detection is employed, suitable exciplex components for use in the present invention comprise monomeric components which when exposed to a first excitation signal, such as a first excitation light signal, avoid undesirable energy transfer which significantly affects the amplitude of the emission at the wavelength of the excited state complex emission. For example, the total integrated intensity at the wavelength of the second emitted signal (i.e., the total integrated intensity at the wavelength of the excited state complex emission) should not have more than ten percent contribution due to monomer emission, more preferably less than five percent contribution.

Preferred sensors for use in the present invention avoid overlap of the exciplex component emission with the emission of the monomeric indicator component(s) which forms the excited state complex. For example, the total integrated intensity at the wavelength of the second emitted signal should not have more than ten percent contribution due to emission of the monomeric indicator component(s), more preferably less than five percent contribution.

For most preferred exciplex components, one of the monomeric components is an electron donor component and the other monomeric component is an electron acceptor component. Most preferred exciplex components further satisfy the following relationship:

$$E^{ox} - E^{red} \leq h\ \nu(hex) + 0.25\ eV$$

where $E^{ox}$ is the ground state oxidation potential of the donor component, $E^{red}$ is the ground state reduction potential of the acceptor component, each measured relative to the same standard, hv (hex) is the maximum energy in eV (electron volts) of the excited state species emission measured in n-hexane, and the donor component and acceptor component are assigned so that the absolute value of $E^{ox} - E^{red}$ is minimized.

For brevity, the excimer component and exciplex component will sometimes be generically referred to as the "excited state complex." Also for brevity, the use of a parenthetical "s" will refer to either the singular or plural of the attached word (e.g., "component(s)" refers to either a single component or a plurality of components).

As noted above, it is important that the excited state complex provided emitted signals be dependent on the concentration of the analyte in the medium, preferably to a greater extent than the other emitted signal or signals from any given sensor of the present invention. Such excited state complex provided emitted signals are preferably dynamically quenchable by the analyte in the medium. The other emitted signal or signals from any given sensor in accordance with the present invention may also be dynamically quenchable by the analyte in the medium.

In one embodiment, the signal or signals emitted from the sensing element preferably result from the sensing element fluorescing. In this embodiment, the Stern-Volmer quenching constant of the excited state complex provided emitted signal is preferably higher than that of the other emitted signal or signals.

The sensors, methods and compositions of the present invention are useful in applications where the analyte is not a dynamic quencher of the emitted signal or signals, but instead, where the analyte concentration can be made to affect the concentration of a messenger species which is capable of dynamically quenching the emitted signal or signals. For example, it is well known in the art that enzymatic reactions involving glucose, adenosine triphosphate (ATP) or cholesterol dependent production or consumption of oxygen enable oxygen optrodes to serve as transducers for detection of these analytes.

Although the monomeric component(s) may be physically mixed or dispersed in a matrix material of the sensing element, it is preferred that the monomeric component(s) be covalently bonded to the matrix material. For example, the monomeric component(s) may be covalently bonded to, and therefore an integral part of, the polymeric material which is preferably included in the matrix material. Although the monomeric component(s) may be part of a polymer molecule which includes more than one monomeric component moiety such monomeric component(s) are still considered monomeric since each such component is capable of providing an emitted signal which is characteristic of the basic indicator compound (monomer) from which it is derived. In contrast, the emitted signal provided by the excimer component produced in the sensing element from two individual monomeric indicator component moieties, for example, on the same polymer molecule and/or on different polymer molecules, has a different characteristic than the emitted signals from the monomeric indicator component(s). Likewise, the emitted signal provided by the exciplex component (e.g., produced from a monomeric indicator component and a monomeric non-indicator component, for example, on the same polymer molecule and/or on different polymer molecules) has a characteristic which is different from the emitted signal provided by the monomeric indicator component.

The excited state complex is preferably produced when an excitation signal is provided to the sensing element. The excited state complex is believed to be inactive and/or to not be produced in the absence of the excitation signal.

In many instances, the covalently bonded monomeric component(s) are each derived from a compound or substance which itself is not suitable to be covalently bonded to the matrix material. In these instances, it may be necessary to derivatize or functionalize such compound and produce a precursor of the monomeric component. This is done by chemically modifying the compound to include at least one group with a functional portion, preferably a functional multiple bond, which functional portion is capable of chemically reacting with the matrix material or precursor of the matrix material to covalently bond the compound thereto. Of course, if the basic compound from which the monomeric component is derived is able to be covalently bonded to the matrix material or matrix material precursor, it is not necessary to further derivitize or functionalize such compound.

The functionalizing of such non-covalently bondable compounds is illustrated by selecting a matrix material comprising a silicone-based polymer and a compound which does not react with the matrix material or matrix material precursor such as a polynuclear aromatic compound. Such polynuclear aromatic compounds include the basic (underivatized) polynuclear aromatic compounds, as well as one or more derivatives thereof, that is one or more derivatives including non-functional groups which do not react with the matrix material or matrix material precursor. Such compounds are not able to be covalently bonded to such silicone-based polymers or their precursors. However, these compounds can be reacted to form attachment groups having a functional portion, such as appropriately configured alkenyl groups, substituted alkenyl groups and the like, which are capable of reacting with and bonding to silicone-based polymers and/or precursors thereof, such as polymethylhydrosiloxanes. In particular, if the silicone-based polymer is to be derived by addition curing, it is preferred to functionalize or derivatize the indicator substance or compound or monomeric compounds to attach one or more alkenyl groups and/or substituted alkenyl groups thereto. Such groups are capable of being hydrosilylated, for example, with a polymethylhydrosiloxane to covalently bond the monomeric component to the silicone-based polymer precursor. The resulting precursor or compound can be reacted with vinyl-terminated polysiloxane, thereby forming an addition-cure silicone including the monomeric component(s).

Any type of group may be attached to the compound, provided that such group comprises a functional portion, preferably a multiple bond, more preferably a carbon-carbon multiple bond and still more preferably a carbon-carbon double bond, which is capable of chemically reacting with a polymer or polymer precursor to form the covalently bonded monomeric component. The group also should have substantially no undue detrimental effect on the analyte sensitivity of the excited state complex provided emitted signal, on the other emitted signal or signals used in making analyte concentration determinations, or on the medium to which the monomeric component is exposed. Preferably, the group is organic in nature. Particularly attractive benefits are obtained when the monomeric indicator component is derived from a monomeric indicator component precursor including at least one indicator compound or substance which has an aromatic ring to which is directly covalently bonded a group with a functional multiple bond which is isolated by a silicon-free chain (i.e., a chain of atoms linking the aromatic ring to the functional multiple bond which includes no silicon atoms), more preferably a chain linking only carbon atoms, from the aromatic ring. Such indicator component precursors are relatively easy to produce and use, and provide sensing elements with very useful properties. In another particularly useful embodiment, the group is a vinyl group covalently bonded directly to an aromatic ring of the indicator compound.

As noted above, particularly useful groups include alkenyl groups; substituted alkenyl groups and the like. Such groups and substituted groups preferably include 2 to about 20 carbon atoms, and may have a terminal double bond, i.e., a double bond associated with the terminal carbon atom. Examples of useful groups include vinyl, allyl, butenyl, hexenyl, heptenyl, octenyl, decenyl and the like groups. The presently useful substituted alkenyl groups include the groups described herein substituted with one or more substituent groups including elements such as oxygen, nitrogen, carbon, hydrogen, silicon, halogen, phosphorus and the like and mixtures and combinations thereof. Thus, the attached group can include at least one heteroatom.

Various chemical modification techniques, many of which are conventional and well known in the art, may be employed to functionalize or derivatize the monomeric compound(s) with the group or groups to produce the monomeric component precursor. Care should be exercised to avoid destroying or even substantially diminishing the analyte sensitivity (e.g., sensitivity to the gas component of interest) and intensity of the presently useful emitted signal or signals in the process of attaching one or more groups. However, it has been found that sufficient sensitivity is maintained if the characteristic structure of the monomeric compound(s) remains substantially unaffected, i.e., intact, after the chemical modification.

In a particularly useful embodiment, the indicator component is sensitive to the concentration of oxygen and comprises one or more polynuclear aromatic compounds and/or one or more derivatives thereof. The polynuclear aromatic compound is preferably any fluorescent or absorbent, more preferably fluorescent, optical indicator of the polynuclear aromatic class. The polynuclear aromatic compound from which the indicator component is derived is still more preferably selected from the group consisting of perylene, decacyclene, benzoperylene (e.g., benzo[ghi] perylene), coronene, pyrene, porphycine, porphyrin, chlorin, phthalocyanine and derivatives and mixtures thereof. Since perylene and derivatives of perylene have a relatively reduced sensitivity to oxygen, other polynuclear aromatic compounds, such as those noted herein, are preferably employed when the analyte is oxygen. When an excimer component is to be utilized, the monomeric indicator component is preferably selected from one polynuclear aromatic compound, derivatives of the same one polynuclear aromatic compound and mixtures thereof. Excellent results are achieved if the polynuclear aromatic compound is benzo [ghi]perylene.

If desired, the basic polynuclear aromatic compound may be derivatized with one or more other groups, e.g., nonfunctional substituent groups such as alkyl groups, provided such derivatization does not substantially interfere with excited state complex provided emitted signal generation. Such derivatives are discussed in Yafuso et at. U.S. Pat. No. 4,849,172 which is hereby incorporated in its entirety by reference herein. One goal of the use of such derivatives is to increase the solubility of the indicator substance in the matrix material. The "covalent bonding" feature described herein mitigates against this solubility constraint. Thus, the basic or underivatized polynuclear aromatic compounds, e.g., as described herein, may be advantageously used to produce the covalently bonded monomeric component(s). When the covalently bonded monomeric indicator component or one or more of the covalently bonded monomeric components is derived from a polynuclear aromatic compound (even an underivatized polynuclear aromatic compound) it is herein considered a derivative of a polynuclear aromatic compound because the polynuclear aromatic compound may include at least a portion of the attached group, noted above, and is derivatized by being covalently bonded to the matrix material. Thus, for example, the monomeric indicator component of a sensing element derived by covalently bonding vinyl benzo[ghi]perylene in an addition cure silicone polymer is said to be a derivative of benzo [ghi]perylene.

The monomeric components useful in the present invention may be selected from any compound or derivatives thereof which is capable of functioning as a monomeric component, as described herein. The monomeric components useful in a given sensor may include, for example, two or more similar monomeric indicator components, two or more different monomeric indicator components, or one or more, preferably one, monomeric indicator components and one or more, preferably one, monomeric non-indicator components. Preferably, such monomeric components have no substantial detrimental effect on the sensing element, on the sensor system, on the analyte or on the medium to which the sensing element is exposed.

Examples of monomeric components which produce more preferred exciplex components include: (1) polynuclear aromatic monomeric components; (2) aliphatic or aromatic amine-containing or aromatic ether-containing monomeric components; and (3) aromatic nitrite monomeric components. More preferred exciplex components comprise at least one monomeric component selected from group (1) and at least one monomeric component selected from group (2). Alternatively, another more preferred exciplex component comprises at least one monomeric component selected from group (3) and at least one monomeric component selected from either group (1) or (2).

Examples of useful aromatic monomeric components (group 1) include biphenyl, naphthalene, phenanthrene, p-terphenyl, chrysene, benzpyrene, pyrene, dibenzanthrene, benzanthrene, anthracene, perylene, benzperylene, fluoranthene, coronene, quinoline, phenylquinoline, benzquinoline, quinoxaline, dibenzquinoxaline, benzquinoxaline, phthalimide, pyridine, phenazine, dibenzphenzine, acridine, benzacridine and derivatives of these compounds. Examples of useful aliphatic or amine-containing or aromatic ether-containing monomeric components (group 2) include tetramethyl-p-phenylenediamine, dimethoxydimethylaniline, methoxydimethylaniline, diethylaniline, diphenylmethylamine, triethylamine, indole, dimethyltoluidine, tri-p-anisylamine, ditolylmethylamine, tritolylamine, triphenylamine, ethylcarbazole, trimethoxybenzene, tetramethoxybenzene and derivatives of these compounds. Examples of aromatic nitrite acceptor monomeric components (group 3) include benzonitrile, cyanonaphthalene, dicyanobenzene and derivatives of these compounds.

Any of these monomeric component pairs can be tethered and/or covalently bonded to a matrix material. Alternatively, freely diffusing monomeric component pairs or their tethered derivatives can be used for sensing applications in free solution.

Preferably, the excimer component and exciplex component producing monomeric component(s) of the present sensing elements are positioned or oriented so as to facilitate excited state complex formation. Thus, these monomeric component(s) can be said to be in enforced association. By "enforced association" it is meant that the monomeric component(s) are positioned or oriented in physical and/or molecular enforcement to promote or facilitate the formation and/or maintenance of a channel or path for excited state complex formation which (a) is kinetically dominant relative to free diffusion, and/or Co) is kinetically competitive with the decay of the excited state complex in the absence of the analyte. Enforced association facilitates the development of sensors based on a wide variety of monomeric components which may not otherwise form appreciable excited state complex at similar concentrations as free monomeric components. Enforced association provides relatively long lived excited state complexes with acceptable Stern-Volmer slopes in cases where the monomeric component(s) themselves are too short lived to be useful. Enforced association may minimize kinetic heterogeneity for excited state complex dissociation, thereby affording more reproducible Stern-Volmer slopes based on: the excited state complex to monomeric component ratio; or the phase shift difference; or the demodulation factor ratio; or the excited state complex emission alone.

Enforced association can be achieved in various ways, for example, by:

1. Intramolecular excited state complex forming molecules dispersed in a matrix material.
2. Intramolecular excited state complex forming molecules covalently attached to a matrix material.
3. Monomeric component aggregates dispersed in or covalently attached to a matrix material or adsorbed, preferably at high loadings, to the surface of a matrix material.
4. Intramolecular excited state complex forming molecules covalently attached, adsorbed or otherwise attached to the surface of a matrix material.

5. An inclusion complex comprising the acceptor (donor) in a supra-molecule having an associated donor (acceptor).
6. Ionic binding of ionically charged monomeric components.

A particularly useful indicator component in enforced association is one which includes a first monomeric indicator component and a second similar monomeric indicator component which are covalently bonded together. Each of these monomeric indicator components may be considered a monomeric indicator component itself since each is capable of emitting a signal in response to being excited, and each is capable of combining with another monomeric indicator component to produce an excimer component. By covalently bonding or tethering the two monomeric indicator components together, the two monomeric indicator components are positioned to have increased accessibility to each other for excimer formation. The covalent link between the two monomeric indicator components is preferably such that the formation of an excimer component from the two covalently linked monomeric indicator components is facilitated. Such covalent link, particularly where each of the monomeric indicator components is a polynuclear aromatic monomeric component, such as described above, preferably includes about 1 to about 20, more preferably about 2 to about 7, atoms, for example, carbon atoms, in the "chain" between the two monomeric indicator components.

The indicator component including the first and second monomeric indicator components, as described above, is preferably further covalently bonded, if at all, to a solid matrix material; through a single covalent linkage. Thus, such preferred tethered indicator components do not include monomeric indicator components which are each separately covalently bonded to a polymeric material, for example, the present matrix material, and not otherwise bonded to each other.

The covalent link (e.g., the chain) between two monomeric indicator components can include one or more functional portions to enable the tethered indicator component to be covalently linked to the solid matrix material. Alternatively, one of the two monomeric indicator components may include a functional portion (separate from the chain between the two monomeric indicator components) to enable the indicator component to be covalently linked to the solid matrix material.

The use of bichromophoric components such as the covalently bonded or tethered indicator components described above, provides for reproducible and reliable analyte concentration determinations by generating reproducible working curves which are independent of bichromophoric component concentration over a broad concentration range.

Another particularly useful embodiment involves two or more different monomeric components at least one of which is a monomeric indicator component, which components are preferably covalently bonded together. The monomeric indicator component is capable of emitting a signal in response to being excited. These monomeric components are further capable of producing an exciplex component. By covalently bonding or tethering the two components together, the monomeric components are positioned to have increased accessibility to each other for exciplex component formation. The covalent link between the monomeric components is preferably such that the formation of an exciplex component from the covalently linked components is facilitated. Such covalent link preferably includes about 1 to about 20, more preferably about 2 to about 7, atoms, for example, carbon atoms, in the chain between the components.

The monomeric components, as described above, are preferably covalently bonded to a solid matrix material. The covalent link (e.g., the chain) between the monomeric components can include one or more functional portions to enable the monomeric components to be covalently linked to the solid matrix material. Alternatively, one of the monomeric components can include a functional portion (separate from the chain between the monomeric components) to enable the indicator component to be covalently linked to the solid matrix material.

The use of combined monomeric components such as the covalently bonded or tethered combined monomeric components described above, provides for reproducible and reliable analyte concentration determinations by generating reproducible working curves which are independent of combined monomeric component concentration over a broad concentration range.

The amount of monomeric component(s) employed in the present systems may vary over a broad range and depends, for example, on the particular monomeric component(s) being employed, on the matrix material employed, on the sensing application involved and the like. Such amount or amounts should be effective to produce the desired excited state complex and to yield the desired signal or signals. For example, the total amount of monomeric component(s) may be in the range of about 0.0001% to about 20% or in the range of about 0.001% to about 10% or more, by weight calculated on the total weight of the sensing element. In many instances, concentrations of less than about 5% or even about 1% or less, by weight calculated on the total weight of the sensing element, provide excellent results. Care should be exercised, for example, if it is desired (as it is preferred) to achieve enforced association, to avoid conditions which result in extended aggregates or extended aggregation of such component or components which can cause additional quenching of the excited state complex emission (independent of the analyte concentration) and/or a reduction in analyte sensitivity of the excited state complex emission.

Any suitable matrix material, preferably a polymeric matrix material, may be employed provided that it functions as described herein. Particularly useful polymeric matrix materials include those based on addition cure silicone polymers. The matrix material, or the precursor thereof, should preferably be such as to chemically react with the precursor or precursors of the monomeric component(s) and produce a sensing element with covalently bonded monomeric component(s).

Although various polymers can be employed as the matrix material, it is preferred that the matrix material be permeable, more preferably highly permeable, to the analyte, for example, a normally gaseous component, of interest so that the sensitivity of the sensing element to the analyte of interest is optimized. If a silicone-based polymer is employed in the matrix material, it may include polymers derived from vinyl terminated polysiloxanes and polyalkyl(aryl)hydrosiloxanes. Such polyalkyl(aryl) hydrosiloxanes include, but are not limited to, those having the formula

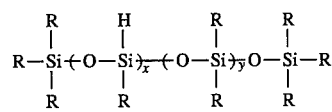

where each of x and y is independently an integer in the range of 1 to about 500 and R is independently selected from the group consisting of H, alkyl, and substituted alkyl, preferably $CH_3$, $CH_2CH_2CF_3$, $CH_2(CH_2)_nCH_3$, and phenyl, where n is an integer in the range of 1 to about 22. Of this group, polymers in which a major portion of the R groups are methyl are preferred because of the high gas permeability of such polymers. A sufficient number of hydride groups should be present to provide a satisfactory cross-linked or cured polymer, and preferably to react with the monomeric component precursor(s) to covalently bond the monomeric component(s) to the matrix material. It is of course realized that other members of the homologous series which include the above-noted polymers may also be used. The final silicone-based matrix material is cross-linked. Suitable vinyl terminated polysiloxanes include two or more functional vinyl groups which react with the hydride or hydro groups of the polyalkyl(aryl)hydrosiloxanes, for example, polymethylhydrosiloxanes, to form the cross-linked matrix material. Such cross-linking advantageously occurs in the presence of a catalyst, such as a platinum-containing catalyst. The properties of the cross-linked silicone can be varied by changing the degree of cross-linking, for example, by adjusting the concentration of the Si-H groups or component on the polyalkyl(aryl)hydrosiloxanes, for example, polymethylhydrosiloxanes and/or the molecular weight of the vinyl-terminated polysiloxanes.

The precursors of the monomeric components useful in the present invention can be obtained using synthesizing procedures, such as formation of aldehydes, Wittig reactions to give vinyl derivatives, and the like. The monomeric component precursor(s) thus obtained can be dispersed in a silicone-based polymer, such as polymethylhydrosiloxane, in a volatile solvent, such as benzene, hexane and the like, and be allowed to react to covalently bond the monomeric component(s) to the silicone-based polymer. The silicone-based polymer, having the chemically attached monomeric component(s), is then reacted, for example, using conventional addition curing, to form the sensing element.

An alternative, and less desirable, method for producing the present sensing element involves combining the precursor or precursors of the monomeric component(s) with the vinyl-terminated polysiloxane, preferably in an inert solvent to promote dissolution of the above-noted precursor or precursors, and any catalyst e.g., platinum group metal, which may be employed. This combination is then mixed with polymethylhydrosiloxane at conditions effective to covalently bond the monomeric component(s) to the matrix material and form the present sensing element.

These and other aspects and advantages of the present invention are set forth in the following detailed description and claims, particularly when considered in conjunction with the accompanying drawings.

DETAILED DESCRIPTION OF THE DRAWINGS

FIG. 1 shows a sensor 10 according to the present invention. Sensor 10 is adapted to determine the concentration or partial pressure of oxygen in blood. An optical fiber 12 is connected to an appropriate light transmitting apparatus 14, which is capable of transmitting light at 395 nanometers. The light transmitting apparatus 14 generates the excitation light at this wavelength. The optical fiber 12 is also connected to a light receiving apparatus 16, which, in turn, is connected to a conventional electronic processor 17.

Located on the optical surface 18 of the optical fiber 12 is a matrix 20 which is an oxygen permeable material, such as a cross-linked addition cured siloxane polymer. Covalently bonded in matrix 20 is about 1.0% by weight of a mixture of vinyl derivatives of benzo[ghi]perylene.

This siloxane polymer is obtained by reacting a polymethylhydrosiloxane, such as those described above in which x is equal to about 10 and y is equal to about 19, with a mixture of vinyl benzo[ghi]perylene derivatives to covalently bond the monomeric benzo[ghi]perylene moieties to the polymethylhydrosiloxane. This modified polymethylhydrosiloxane is then reacted with a vinyl terminated polysiloxane in the presence of a platinum catalyst to form a cross-linked siloxane polymer including covalently bonded monomeric benzo[ghi]perylene moieties. The vinyl terminated polysiloxane has the following formula

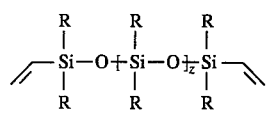

where z is about 376 and each R is methyl. The ratio of SiH to vinyl in the crosslinking reaction is controlled to provide a suitable cross-linked elastomer product.

The highly oxygen permeable matrix 20 adheres to the optical surface 18 and slightly down along the sides 22 of the end of fiber 12, An opaque overcoating 24, comprising iron oxide pigment dispersed in an addition cured polysiloxane, can then be applied over the totality of the matrix 20 and down further along the side 22 of the fiber 12.

In use, sensor 10 functions as follows. The tip of optical fiber 12 including matrix 20 and overcoating 24 is exposed or immersed in blood, the oxygen concentration of which is to be determined. Light transmitting apparatus 14 transmits light at 395 nanometers to the optical fiber 12. The excitation light at 395 nanometers causes the matrix 20 to fluoresce at two separate wavelengths, 421 nanometers and 460 nanometers. The emission at the first or shorter wavelength is the result of the excitation of monomeric benzo[ghi]perylene moieties in matrix 20. The emission at the second or longer wavelength is the result of an excimer which is formed by the interaction of one or more excited monomeric benzo[ghi]perylene moieties in matrix 20 and one or more unexcited (or ground state) benzo[ghi]perylene moieties in matrix 20. Both the emissions at 421 nanometers and 460 nanometers are dependent on the concentration of oxygen in the blood with the longer wavelength emission being more so dependent than the emission at 421 nanometers.

The fluorescent emitted signals are transmitted from matrix 20 through optical fiber 12 to light receiving apparatus 16. Processor 17 uses information received by light receiving apparatus 16 on the longer emitted signal to determine a value of the oxygen concentration in the blood. Receipt and analysis of this fluorescent light by light receiving apparatus 16 and processor 17 is carried out in a manner similar to that described in the above-referenced Lubbers, et at. patent and in Heitzmann U.S. Pat. No. 4,557,900 each of which is incorporated in its entirety herein by reference.

Processor 17 uses information received by light receiving apparatus 16 of the fluorescent signal emitted at 421 nanometers to develop a ratio of the emitted fluorescent signal at 460 nanometers to the fluorescent signal at 421 nanometers. Using this ratio together with the above-noted oxygen concentration, processor 17 can determine a corrected concentration of oxygen in the blood to be analyzed. This corrected oxygen concentration is found to be accurate even if the optical fiber 12 is bent at one or more points along its length and/or if other light transmission difficulties are encountered.

The above-noted procedure may occur periodically or even substantially continuously to give substantially continuous oxygen concentration results. Of course, the transmission of the emission at 421 nanometers can take place before transmission of the emission at 460 nanometers. Also, by proper selection of the optical indicators, e.g., fluorescent dyes, the concentration of other components of interest can be determined. In addition, media other than blood can be analyzed.

The optical fiber 12 may be in the form of a probe or a catheter insertable into a blood vessel of a patient to provide continuous on-line in vivo monitoring of oxygen concentration in the blood. Alternately, the present sensor can be embodied in a flow-through housing as shown, for example, in the above-referenced Heitzmann patent, to provide extra corporeal monitoring of oxygen concentration in the blood.

In an additional embodiment, the matrix 20 is a highly oxygen permeable material, such as a cross-linked, siloxane-based polymer, and includes about 1.0% by weight of an indicator component derived from vinyl benzo[ghi]perylene covalently bonded to the polymer and about 1.0% by weight of vinyl perylene covalently bonded to the polymer. The opaque overcoating 24, comprises a mixture of carbon black and cellulosic material.

In use, this alternate embodiment of sensor 10 functions as follows. The tip of optical fiber 12 including matrix 20 and overcoating 24 is exposed or immersed in blood, the oxygen concentration of which is to be determined. Light transmitting apparatus 14 transmits light at 395 nanometers to the optical fiber 12. The excitation light at 395 nanometers causes the matrix 20 to fluoresce, which is believed to result in part from an excited state complex of benzo[ghi]perylene functionalities or moleties. The lifetime of this fluorescent signal, at a wavelength of about 450 nanometers, is longer than about 50 nanoseconds. A fluorescent signal is transmitted from matrix 20 through optical fiber 12 to light receiving apparatus 16. This fluorescent signal, derived from excitation light at 395 nanometers, depends on the concentration of oxygen in the blood being analyzed. Processor 17 uses information received by light receiving apparatus 16 on this fluorescent signal to determine a value of the oxygen concentration in the blood.

In a further additional embodiment, the matrix 20 is a highly oxygen permeable material, such as a cross-linked, siloxane-based polymer, and includes about 1.0% by weight of an indicator component derived from allyl benzo[ghi] perylene covalently bonded to the polymer and about 1.0% by weight of allyl perylene covalently bonded to the polymer. The opaque overcoating 24 comprises a mixture of carbon black and cellulosic material.

In use, this further alternative embodiment of sensor 10 functions as follows. The tip of optical fiber 12 including matrix 20 and overcoating 24 is exposed or immersed in blood, the oxygen concentration of which is to be determined. Light transmitting apparatus 14 transmits light at 395 nanometers to the optical fiber 12. The excitation light at 395 nanometers causes the matrix 20 to fluoresce, which emission is believed to result in part from an excited state complex of benzo[ghi]perylene functionalities or moieties. The lifetime of this fluorescent signal, at a wavelength of about 450 nanometers, is longer than about 50 nanoseconds. A fluorescent signal is transmitted from matrix 20 through optical fiber 12 to light receiving apparatus 16. This fluorescent signal, derived from excitation light at 395 nanometers, depends on the concentration of oxygen in the blood being analyzed. Processor 17 uses information received by light receiving apparatus 16 on this fluorescent signal to determine a value of the oxygen concentration in the blood.

Figure 2:
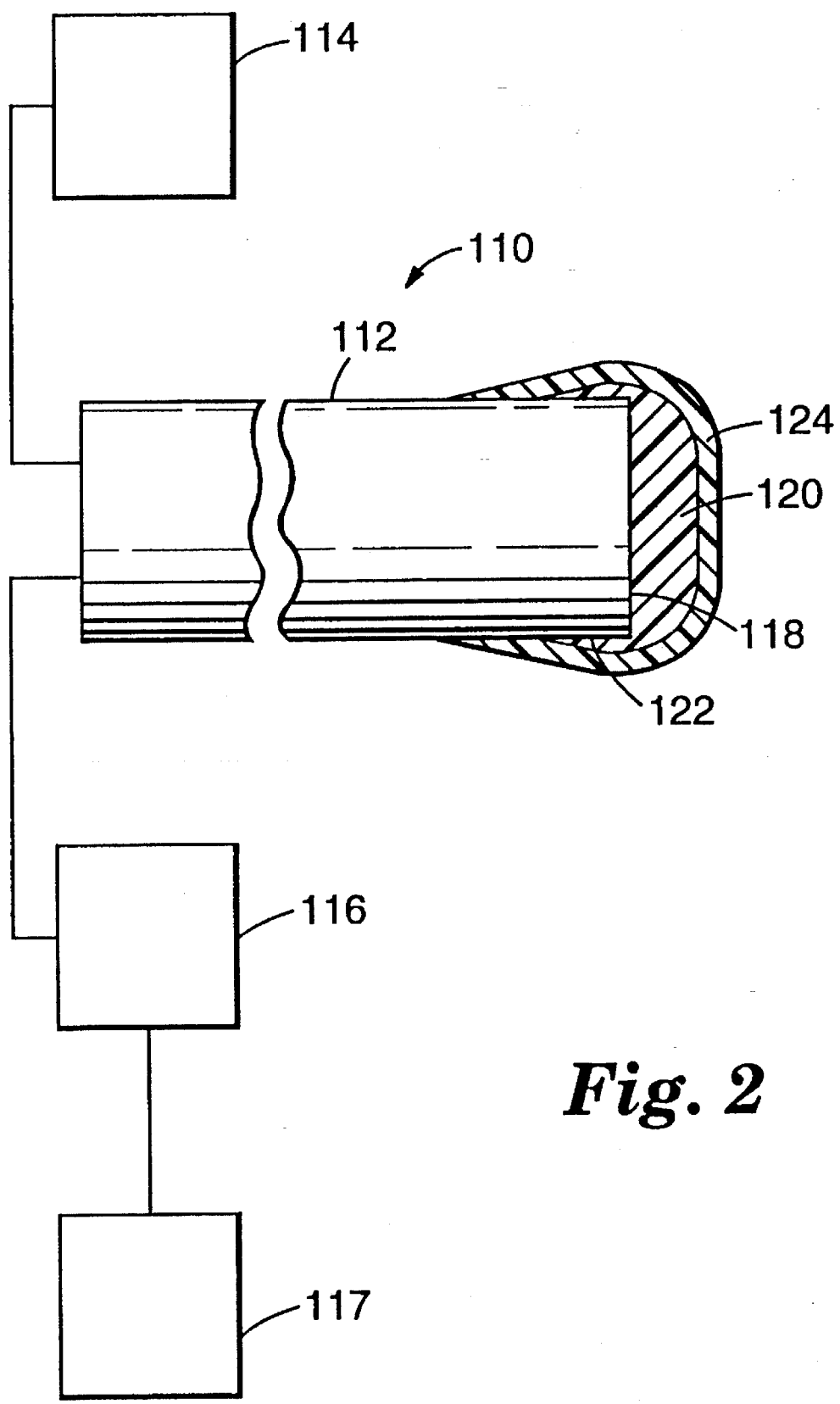
FIG. 2 is a schematic illustration of an alternate embodiment of the sensor apparatus according to the present invention.

An alternate embodiment, which is described with reference to FIG. 2, involves a sensor apparatus making use of intensity modulated (sine wave) signals in the MHz range.

In this embodiment, sensor 110 is adapted to determine the concentration or partial pressure of oxygen in blood. An optical fiber 112 is connected to an appropriate light transmitting apparatus 114, which is capable of transmitting intensity modulated (sine wave) light in the MHz range. The light transmitting apparatus 114 generates the modulated excitation light at this frequency. The optical fiber 112 is also connected to a light receiving apparatus 116, which, in turn, is connected to a conventional electronic processor 117.

The light transmitting apparatus 114 includes a frequency generator (one or more frequencies simultaneously) linked to an electrically controlled light emitting structure, such as a light emitting diode, a frequency doubled light emitting diode, or a combination of elements such as a continuous wave laser or incandescent light source coupled to an acoustooptic modulator or electrooptic modulator, and the like.

The light receiving apparatus 116 includes a highly sensitive light detector having a rapid response time. Suitable detectors include photomultiplier tubes such as those sold under the trademark R928 by Hamamatsu Photonits K.K., Hamamatsu, Japan, as well as avalanche photodiodes and microchannel plates, also available from the same supplier. Using techniques well known in the art, heterodyne detection can be implemented by modulating the detector sensitivity at a frequency, equal to the fundamental modulation frequency, $F_f$ in the MHz regime, plus or minus a heterodyne modulation frequency $F_h$ in the Hz or kHz region.

The processor 117 may include, for example, an analog to digital converter coupled by a direct memory access device to a computer, or an analog phase comparator circuit known to those skilled in the art, and the like. The SLM 48000MHF Fourier Transform Spectrofluorometer manufactured by SLM-Aminco in conjunction with an argon ion laser provides frequency modulated light generation, light receiving apparatus and processor capability to perform the methods outlined herein; to measure phase shifts, demodulation factors, or both at either a single modulation frequency or simultaneously at several modulation frequencies. Commercial software is available to apply a well-known digital fast Fourier transform to the data and to interpret phase and demodulation data at multiple modulation frequencies in terms of a distribution of emission lifetimes and relative contributions. This enables determination of the contribution of the excited state complex and monomeric indicator component provided emitted signals to the total phase shift and/or demodulation factors at each wavelength, even when several overlapping emission signals are present.

Located on the optical surface 118 of the optical fiber 112 is a matrix 120 which is an oxygen permeable material, such as a cross-linked addition cured siloxane polymer which is similar to the polymer described previously. Dispersed in the polymer is 0.004% by weight of 1,3-bis-(1-pyrene)propane commercially available through Molecular Probes Inc.

The highly oxygen permeable matrix 120 adheres to the optical surface 118 and slightly down along the sides 122 of the end of fiber 112. An opaque overcoating 124, comprising iron oxide pigment dispersed in an addition cured polysiloxane, can then be applied over the totality of the matrix 120 and down further along the side 122 of the fiber 112.

In use, sensor 110 functions as follows. The tip of optical fiber 112 including matrix 120 and overcoating 124 is exposed or immersed in blood, the oxygen concentration of which is to be determined. Light transmitting apparatus 114 transmits light at 10 MHz and 325 nm to the optical fiber 112. This excitation light causes the matrix 120 to fluoresce at two separate wavelengths, 375 nanometers and 500 nanometers. Both fluorescent emissions are sine wave modulated. The emission at the first or shorter wavelength is believed to be the result of the emission from monomeric pyrene moieties in matrix 120. The emission at the second or longer wavelength is the result of an excimer which is formed by the interaction of one or more excited monomeric pyrene moieties in matrix 120 and one or more unexcited (or ground state) pyrene moieties in matrix 120.

The fluorescent emitted signals are transmitted from matrix 120 through optical fiber 112 to light receiving apparatus 116. Processor 117 uses information received by light receiving apparatus 116 on the emitted signals to determine the extent of the phase shift between and/or the ratio of demodulation factors of these two emitted signals. The extent of this phase shift and/or this ratio of demodulation factors are dependent on the concentration of oxygen in the blood. Thus, by determining the extent of this phase shift and/or this ratio of demodulation factors, values of the oxygen concentration in the blood can be obtained.

Alternately, or as a check on the oxygen concentrations obtained by analyzing the two emission signals, processor 117 can use information received from the light transmitting apparatus 114 on the excitation light and information received by light receiving apparatus 116 on the excimer-derived emitted signal to determine the extent of the phase shift and/or the magnitude of relative demodulation between this emitted signal and the excitation signal. The extent of this phase shift and/or this magnitude of relative demodulation are dependent on the concentration of oxygen in the blood. Thus, by determining the extent of this phase shift and/or this magnitude of relative demodulation, values for the oxygen concentration in the blood can be obtained.

Transmission, receipt and analysis of these modulated signals by light transmitting apparatus 114, light receiving apparatus 116 and processor 117 may be carried out using equipment and in a manner similar to that described in Gratton U.S. Pat. No. 4,840,485 which is incorporated in its entirety herein by reference.

The above-noted procedure may occur periodically or even substantially continuously to give substantially continuous oxygen concentration results. Of course, by proper selection of the optical indicators, e.g., fluorescent dyes, the concentration of other components of interest can be determined. In addition, media other than blood can be analyzed.

The optical fiber 112 may be in the form of a probe or a catheter insertable into a blood vessel of a patient to provide continuous on-line in vivo monitoring of oxygen concentration in the blood. Alternately, the present sensor can be embodied in a flow-through housing as shown, for example, in the above-referenced Heitzmann patent, to provide extra corporeal monitoring of oxygen concentration in the blood.

Figure 3:
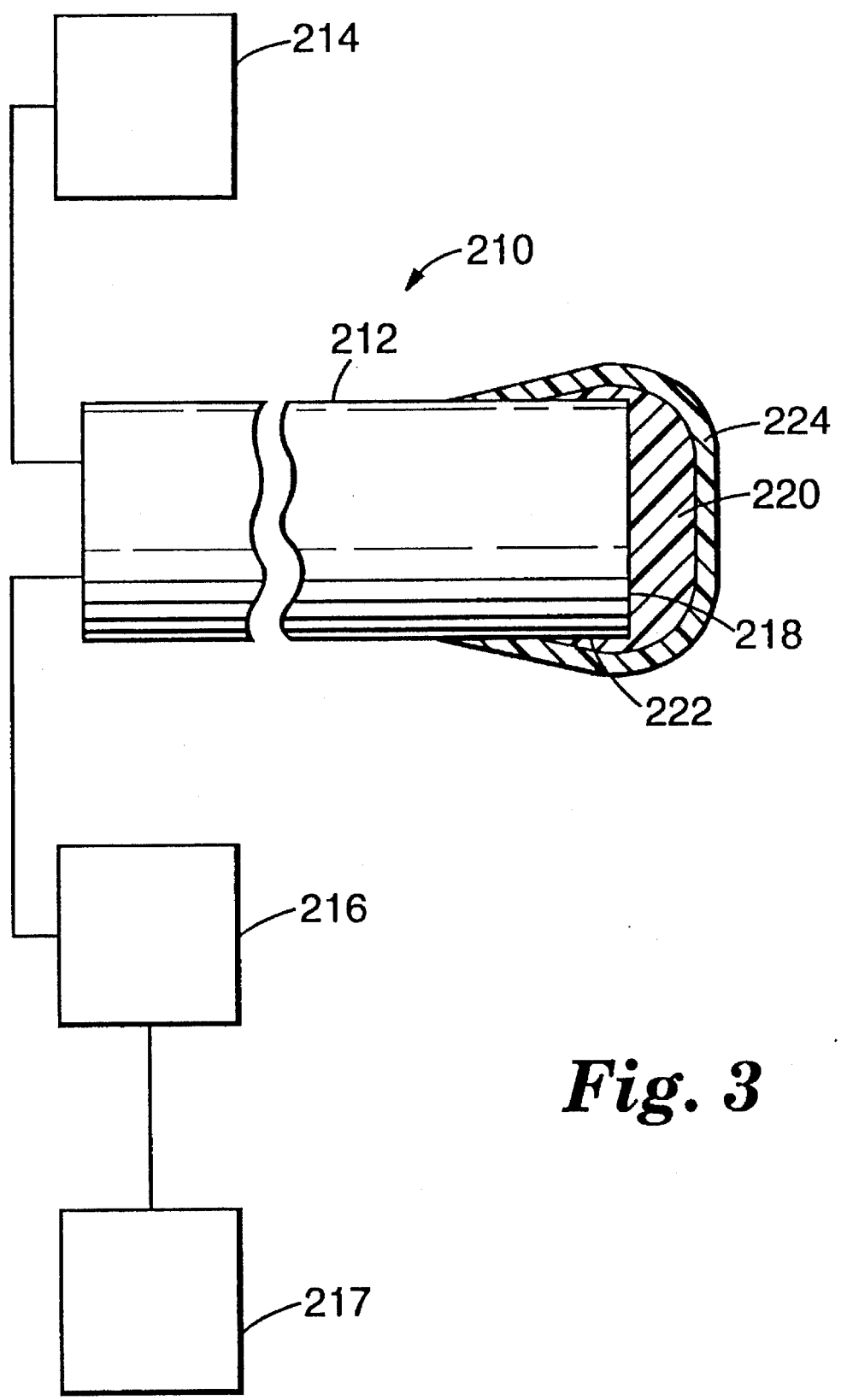
FIG. 3 is a schematic illustration of an alternate embodiment of the sensor apparatus according to the present invention.

FIG. 3 shows a sensor 210 according to the present invention. Sensor 210 is adapted to determine the concentration or partial pressure of oxygen in blood. An optical fiber 212 is connected to an appropriate light transmitting apparatus 214, which is capable of transmitting light at 285 nanometers. The light transmitting apparatus 214 generates the excitation light at this wavelength. The optical fiber 212 is also connected to a light receiving apparatus 216, which, in turn, is connected to a conventional electronic processor 217.

Located on the optical surface 218 of the optical fiber 212 is a matrix 220 which is an oxygen permeable material, such as a cross-linked addition cured siloxane polymer. Dispersed in matrix 20 is about 0.01% by weight of 1-(1-naphthyl)-2-(diethylamino) ethane.

This siloxane polymer is obtained by mixing a polymethylhydrosiloxane, such as those described above in which x is equal to about 10 and y is equal to about 19, with a vinyl terminated polysiloxane and a hydrocarbon solution of 1-(1-naphthyl)-2-(diethylamino) ethane in the presence of a platinum catalyst to form a cross-linked siloxane polymer including dispersed 1-(1-naphthyl)-2-(diethylamino) ethane moieties. The vinyl terminated polysiloxane has the following formula

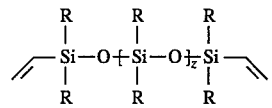

where z is about 78 and each R is methyl. The ratio of SiH to vinyl in the crosslinking reaction is controlled to provide a suitable cross-linked elastomer product. The crosslinking reaction is followed by vacuum drying to remove residual hydrocarbon solvent.

The highly oxygen permeable matrix 20 adheres to the optical surface 218 and slightly down along the sides 222 of the end of fiber 212. An opaque overcoating 224, comprising iron oxide pigment dispersed in an addition cured polysiloxane, can then be applied over the totality of the matrix 220 and down further along the side 222 of the fiber 212.

In use, sensor 210 functions as follows. The tip of optical fiber 212 including matrix 220 and overcoating 224 is exposed or immersed in blood, the oxygen concentration of which is to be determined. Light transmitting apparatus 214 transmits light at 285 nanometers to the optical fiber 212. The excitation light at 285 nanometers causes the matrix 220 to fluoresce at two separate wavelengths, 308 nanometers and 420 nanometers. The emission at the first or shorter wavelength is the result of the excitation of monomeric naphthalene moieties in matrix 220. The emission at the second or longer wavelength is the result of an exciplex which is formed by the interaction of an excited monomeric naphthalene moiety in matrix 220 and one or more unexcited (or ground state) triethylamine moieties in matrix 220. Both the emissions at 308 nanometers and 420 nanometers are dependent on the concentration of oxygen in the blood with the longer wavelength emission being more so dependent than the emission at 308 nanometers.

The fluorescent emitted signals are transmitted from matrix 220 through optical fiber 212 to light receiving apparatus 216. Processor 217 uses information received by light receiving apparatus 216 on the longer emitted signal to determine a value of the oxygen concentration in the blood. Receipt and analysis of this fluorescent light by light receiving apparatus 216 and processor 217 is carried out in a manner similar to that described in the above-referenced Lubbers, et al. patent and in Heitzmann U.S. Pat. No. 4,557,900.

Processor 217 uses information received by light receiving apparatus 216 of the fluorescent signal emitted at 308 nanometers to develop a ratio of the emitted fluorescent signal at 420 nanometers to the fluorescent signal at 308 nanometers. Using this ratio together with the above-noted oxygen concentration, processor 217 can determine a corrected concentration of oxygen in the blood to be analyzed. This corrected oxygen concentration is found to be accurate even if the optical fiber 212 is bent at one or more points along its length and/or if other light transmission difficulties are encountered.

The above-noted procedure may occur periodically or even substantially continuously to give substantially continuous oxygen concentration results. Of course, the transmission of the emission at 308 nanometers can take place before transmission of the emission at 420 nanometers. Also, by proper selection of the optical indicators, e.g., fluorescent dyes, the concentration of other components of interest can be determined. In addition, media other than blood can be analyzed.

The optical fiber 212 may be in the form of a probe or a catheter insertable into a blood vessel of a patient to provide continuous on-line in vivo monitoring of oxygen concentration in the blood. Alternately, the present sensor can be embodied in a flow-through housing as shown, for example, in the above-referenced Heitzmann patent, to provide extra corporeal monitoring of oxygen concentration in the blood.

Figure 4:
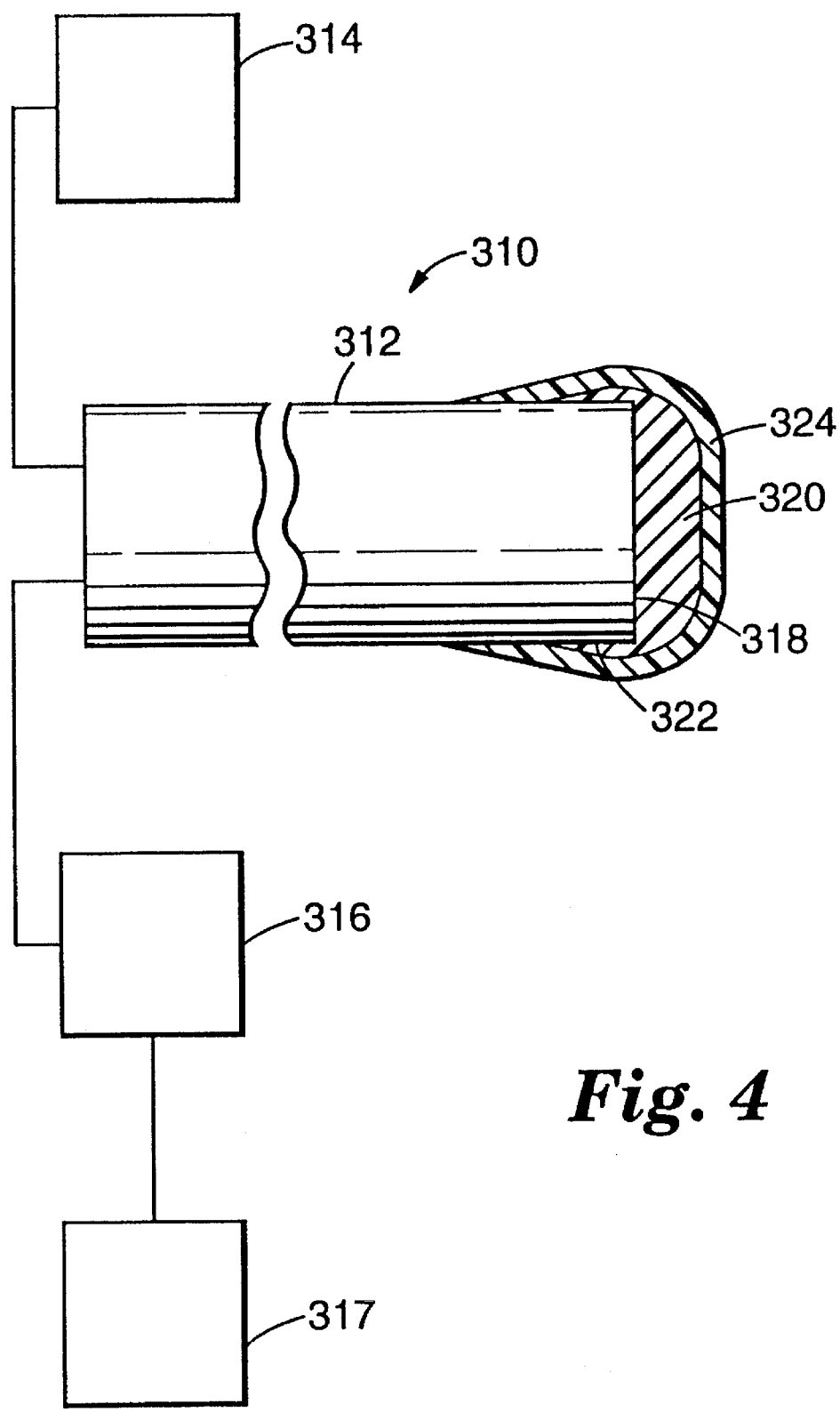
FIG. 4 is a schematic illustration of an alternate embodiment of the sensor apparatus according to the present invention.

An alternate embodiment, which is described with reference to FIG. 4, involves a sensor apparatus making use of intensity modulated (sine wave) signals in the MHz range.

In this embodiment, sensor 310 is adapted to determine the concentration or partial pressure of oxygen in blood. An optical fiber 312 is connected to an appropriate light transmitting apparatus 314, which is capable of transmitting intensity modulated (sine wave) light in the MHz range. The light transmitting apparatus 314 generates the modulated excitation light at this frequency. The optical fiber 312 is also connected to a light receiving apparatus 316, which, in turn, is connected to a conventional electronic processor 317.

The light transmitting apparatus 314 includes a frequency generator (one or more frequencies simultaneously) linked to an electrically controlled light emitting structure, such as a light emitting diode, a frequency doubled light emitting diode, or a combination of elements such as a continuous wave laser or incandescent light source coupled to an acoustooptic modulator or electrooptic modulator, and the like.

The light receiving apparatus 316 includes a highly sensitive light detector having a rapid response time. Suitable detectors include photomultiplier tubes such as those sold under the trademark R928 by Hamamatsu Photonics K.K., Hamamatsu, Japan, as well as avalanche photodiodes and microchannel plates, also available from the same supplier. Using techniques well known in the art, heterodyne detection can be implemented by modulating the detector sensitivity at a frequency, equal to the fundamental modulation frequency, $F_f$ in the MHz regime, plus or minus a heterodyne modulation frequency $F_h$ in the Hz or kHz region.

The processor 317 may include, for example, an analog to digital converter coupled by a direct memory access device to a computer, or an analog phase comparator circuit known to those skilled in the art, and the like. The SLM 48000MHF Fourier Transform Spectrofluorometer manufactured by SLM-Aminco in conjunction with an argon ion laser provides frequency modulated light generation, light receiving apparatus and processor capability to perform the methods outlined herein; to measure phase shifts, demodulation factors, or both at either a single modulation frequency or simultaneously at several modulation frequencies. Commercial software is available to apply a well-known digital fast Fourier transform to the data and to interpret phase and demodulation data at multiple modulation frequencies in terms of a distribution of emission lifetimes and relative contributions. This enables determination of the contribution of the exciplex component and monomeric indicator component provided emitted signals to the total phase shift and/or demodulation factors at each wavelength, even when several overlapping emission signals are present.

Located on the optical surface 318 of the optical fiber 312 is a matrix 320 having a composition similar to matrix 220.

The highly oxygen permeable matrix 320 adheres to the optical surface 318 and slightly down along the sides 322 of the end of fiber 312. An opaque overcoating 324, comprising iron oxide pigment dispersed in an addition cured polysiloxane, can then be applied over the totality of the matrix 320 and down further along the side 322 of the fiber 312.

In use, sensor 310 functions as follows. The tip of optical fiber 312 including matrix 320 and overcoating 324 is exposed or immersed in blood, the oxygen concentration of which is to be determined. Light transmitting apparatus 314 transmits light at 10 MHz to the optical fiber 312. This excitation light causes the matrix 320 to fluoresce at two separate wavelengths. Both fluorescent emissions are sine wave modulated. Again the emission at the first or shorter wavelength is believed to be the result of the emission from monomeric naphthalene moieties in matrix 320. The emission at the second or longer wavelength is the result of an exciplex component which is formed by the interaction of one or more excited monomeric naphthalene moieties in matrix 320 and one or more unexcited (or ground state) triethylamine moieties in matrix 320.

The fluorescent emitted signals are transmitted from matrix 320 through optical fiber 312 to light receiving apparatus 316. Processor 317 uses information received by light receiving apparatus 316 on the emitted signals to determine the extent of the phase shift between and/or the ratio of demodulation factors of these two emitted signals. The extent of this phase shift and/or this ratio of demodulation factors are dependent on the concentration of oxygen in the blood. Thus, by determining the extent of this phase shift and/or this ratio of demodulation factors, values of the oxygen concentration in the blood can be obtained.

Alternately, or as a check on the oxygen concentrations obtained by analyzing the two emission signals, processor 317 can use information received from the light transmitting apparatus 314 on the excitation light and information received by light receiving apparatus 316 on the exciplex-derived emitted signal to determine the extent of the phase shift and/or the magnitude of the relative demodulation between this emitted signal and the excitation signal. The extent of this phase shift and/or this magnitude of relative demodulation are dependent on the concentration of oxygen in the blood. Thus, by determining this extent of phase shift and/or this magnitude of relative demodulation, values for the oxygen concentration in the blood can be obtained.

Transmission, receipt and analysis of these modulated signals by light transmitting apparatus 314, light receiving apparatus 316 and processor 317 may be carded out using equipment and in a manner similar to that described in Gratton U.S. Pat. No. 4,840,485.

The above-noted procedure may occur periodically or even substantially continuously to give substantially continuous oxygen concentration results. Of course, by proper selection of the optical indicators, e.g., fluorescent dyes, the concentration of other components of interest can be determined. In addition, media other than blood can be analyzed.

The optical fiber 312 may be in the form of a probe or a catheter insertable into a blood vessel of a patient to provide continuous on-line in vivo monitoring of oxygen concentration in the blood. Alternately, the present sensor can be embodied in a flow-through housing as shown, for example, in the above-referenced Heitzmann patent, to provide extra corporeal monitoring of oxygen concentration in the blood.

EXAMPLES

The following non-limiting Examples illustrate certain aspects of the invention.

Fluorescence data were obtained on a SPEX Fluorolog Fluorometer, equipped with a 450W Xe lamp, single excitation monochromator blazed at 250 nm, double emission monochromator blazed at 500 nm. Typical slit widths were 0.5 mm or less corresponding to bandwidths on the order of 1 to 2 nm. Emission spectra were corrected and zeroed, excitation spectra were obtained in the ratio mode and were corrected. For variable (oxygen concentration) studies, films were placed in a flow-through chamber equipped with glass or quartz windows. The chamber volume was small to allow for fast gas exchange. The spectra were taken in a front-face mode with excitation normal to the film and emission collected at 22° to the film normal.

Phase modulation experiments were performed using a modified version of the commercially available SLM 48000 Frequency-Domain Fluorometer with single frequency acquisition or with Multi-Harmonic Fourier (MHF) Parallel Acquisition. The SLM 48000 sample chamber was modified by replacing the cuvette holder mount with an x, y, z translator. The proximal terminus of the fiber optic was positioned with the translator at the focal point of the excitation beam (which is focussed with a f/2 lens) such that it was perpendicular to the line of propagation of the excitation. Typically, 200, 600 or 1000 microns core diameter quartz multi-mode fiber optic cables (General Fiber Optics) were used to carry excitation to the sample chamber, and a second fiber of the same core diameter was used to carry emission to the detector. The fibers were cladded with black, electrical cladding to minimize false light effects. The fiber termini were polished and adapted with a Amphenol-type connector on the spectrometer end and a stainless steel capillary tube on the sample end.

EXAMPLE 1

Into a clean dry 500 ml round-bottom flask fitted with a drying tube, a rubber septum and a magnetic stirrer was added 3.2 g of benzo[ghi]perylene and 400 ml of dichloromethane under a blanket of dry nitrogen. When the crystals had dissolved, the solution was cooled to 10° C. Using a 10 ml syringe, 7.5 g of tin(IV)tetrachloride was added. The mixture was made homogenous by stirring, then 4.5 g of dichloromethyl methyl ether was added over 2 minutes. The mixture became blue purple and viscous. The viscosity dropped after about 30 minutes of stirring. The reaction was complete after about 150 minutes. The reaction mixture was quenched with 600 ml of 2N HCl and the product extracted with 600 ml of dichloromethane. The organic layer was washed with 600 ml of water and dried over anhydrous sodium sulfate. The organic phase was passed through a 88.9 mm×50.8 mm silica gel plug, and the product, benzo[ghi]perylene aldehyde in good yield and purity, was separated from the solvent with a rotary evaporator.

EXAMPLE 2

2.7 g of methyl iodide and 4.5 g of 4-(diisopropylaminomethyl)triphenyl phosphine in 10 ml of toluene were allowed to react in a 50 ml round-bottom flask equipped with a magnetic stirrer with stirring overnight at room temperature under dry nitrogen. The reaction mixture formed two phases. The toluene was removed by rotary evaporation. To the remaining mixture was added 12 mmols of lithium diisopropyl amide in anhydrous tetrahydrofuran at 0° C. and stirred for 30 minutes at this temperature. This mixture was added to 3.1 g of benzo[ghi]perylene aldehyde dissolved in 300 ml of anhydrous tetrahydrofuran under an inert atmosphere (dry nitrogen or argon) at 0° C. The reaction was over in an hour, at which time the solvent was removed by rotary evaporation. The residue was dissolved in 500 ml of toluene and washed with two 100 ml portions of 0.50M HCl followed by a water wash and an aqueous 2.5% sodium bicarbonate wash. The organic phase was dried over sodium sulfate. The dry organic phase was stirred with 2 g of activated charcoal, then chromatographed on a 76.2 mm×25.4 mm silica gel column that had been deactivated with ethanol. The product was eluted from the column with toluene. The product, a mixture of vinyl benzo[ghi]perylene isomers, was recovered by rotary evaporation of the solvent and stored in an amber bottle under nitrogen.

EXAMPLE 3

In a nitrogen purged 50 ml round-bottom flask equipped with a magnetic stirrer was placed the vinylbenzo[ghi] perylene product from Example 2 (131 mg), polymethylhydrosiloxane (1.0 g; sold by Petrarch Systems under the trademark PS123), and benzene (30 ml). Platinum catalyst (150 microliters diluted to 10% in hexane; sold by Petrarch Systems under the tradename PC075) was added at room temperature, and the reaction was brought to a gentle reflux. The reaction was determined to be complete by thin layer chromography, using a hexane/ether ($^{90}/_{10}$) mobile phase, when the yellow fluorescent spot (vinylbenzo[ghi]perylene; $R_f$=0.5) was no longer present. The benzene was removed by rotary evaporation and replaced by hexane (30 ml). Subsequent to rotoevaporation of the hexane, the yellow oil was redissolved in hexane (30 ml) and decolorizing carbon (400 mg; sold by J.T. Baker Chemical Company under the trademark Darco G-60) was added. The mixture was gently stirred for 20 minutes then filtered using celite as an aid. Following rotoevaporation of the solvent, the product was adjusted to the appropriate concentration using hexane. This solution was then combined with a vinyl terminated siloxane and platinum catalyst to form an immobilized, cross-linked fluorescent silicone rubber.

The resulting cross-linked fluorescent silicone rubber includes an effective amount of chemically bound, non-leachable monomeric benzo[ghi]perylene moiety, and is effective as a sensing element in an in vivo blood oxygen sensor in accordance with the present invention, for example, as matrix 20 in sensor 10, as described above.

EXAMPLE 4

A series of addition cure silicone elastomers containing covalently bonded benzo[ghi]perylene moieties, derived from vinyl benzo[ghi] perylene were produced. The basic elastomer (run #1) had substantially the same composition as matrix 20 except that the vinyl terminated polysiloxane used was such that z equaled about 78. Two other similar elastomers were produced except that one elastomer (run #2) contained only 10% of the benzo[ghi] perylene moieties as did the basic elastomer, and another elastomer (run #3) contained only 1% of the benzo[ghi] perylene moieties as did the basic elastomer.

Each of these elastomers was tested for fluorescent emission intensity upon being exposed to nitrogen gas containing varying oxygen concentrations and being excited with light at 395 nm. Emissions were monitored at 420 nm (believed to result from the monomeric benzo[ghi]perylene moieties) and at 450 nm or 480 nm (believed to result from excimer produced by the benzo[ghi]perylene moieties). Ratios of the intensities of various emissions were determined.

Results of these tests were as follows:

| Run # | O₂ concentration, (partial pressure) mm | Ratio[1] 480/420 | Ratio[1] 450/420 |
|---|---|---|---|
| 1 | 0 | 1 | 1 |
|   | 160 | 1.27 | 1.18 |
| 2 | 0 | 1 | 1 |
|   | 160 | 1 | 1.11 |
| 3 | 0 | 1 | 1 |
|   | 160 | 1 | 1 |

[1]Ratio equals $(E/M)_o/(E/M)$ where $(E/M)_o$ is the ratio of the intensities of the excimer and monomer measured under nitrogen and (E/M) is the ratio of the intensities of the excimer and monomer measured at the oxygen concentration listed.

These results indicate that the excimer/monomer emission intensity ratio is dependent on the oxygen concentration when the concentration of monomeric indicator component is relatively high. Thus, at relatively high monomeric indicator component concentrations this emission intensity ratio can be used in determining oxygen concentration.

EXAMPLE 5

This is an example of the preparation of a film containing an intramolecular excimer component-forming moiety. To 0.50 g of a vinyl terminated siloxane (sold by Petrarch Systems under the trademark PS441) were added 0.05 g of a polymethylhydrosiloxane (sold by Petrarch Systems under the trademark PS123), 0.50 ml of a $9\times10^{-5}$M $CH_2Cl_2$ solution of 1,3-bis-(1-pyrene)propane, and 10 microliters of Pt catalyst solution. The Pt catalyst solution used in these preparations was a solution of Karsted's catalyst in hexane. The solvents used were spectral grade, dried over molecular sieves. 1,3-bis-(1-pyrene) propane was purchased from Molecular Probes, Inc., Eugene, Oreg.

The mixture was agitated and poured into a 57 mm diameter aluminum weighing pan and allowed to dry and cure in air, then further dried under vacuum overnight to remove residual solvent. The films thus obtained are optically clear.

The response of this film to oxygen was determined in the intensity mode. Upon being excited at 345 nm, excimer emission was monitored at 500 nm and monomer emission at 375 nm. Both excimer emission and monomer emission were dynamically quenchable by oxygen. When plotted in Stern-Volm there was obvious curvature of the excimer oxygen dependence. However, the excimer/monomer ratio in a Stern-Volmer treatment produced a linear response with a slope of 0.0125 mm$^{-1}$.

EXAMPLE 6

The response of the film produced in Example 5 was determined in phase. The film was placed in a thermostated optical isolation chamber equipped with a port for collinear excitation and emission optical fibers and ports for rapid gas exchange. The fiber optic port was positioned to allow the distal fiber termini to provide for excitation and emission collection at an angle of 45 degrees from the film surface to minimize scatter. The film was excited at 325 nm using monochromatic excitation provided from an argon ion laser (Coherent Model 90-6). Emission wavelengths of 500 nm for excimer emission and 375 nm for monomer emission were serially selected using a standard monochromator. The sensor film was exposed to oxygen in nitrogen mixtures with the following composition (volume % oxygen=0.0, 5.09, 10.35, 15.37, and air).

Uncorrected phase shifts were obtained from MHF or from single frequency data. These phase shifts were referenced to the excitation source phase and included phase offsets associated with the electronics and optics. For a modulation frequency of 10 MHz, uncorrected phase data, the difference between the excimer and monomer phase measurements, and the resultant Stern-Vomer slope for oxygen quenching of the excimer fluorescence deconvolved from the kinetics for indirect excimer population were as follows:

| mm O₂ | 0.00 | 38.7 | 78.7 | 117 | 159 |
|---|---|---|---|---|---|
| excimer phase | 244.41 | 228.54 | 221.34 | 215.22 | 219.04 |
| monomer phase | 169.73 | 159.27 | 157.09 | 154.54 | 164.82 |
| phase difference | 74.68 | 69.27 | 64.25 | 60.60 | 54.22 |
| $\tau_o/\tau = \tan\Delta\theta_o/\tan\Delta\theta$ | 1.00 | 1.38 | 1.76 | 2.05 | 2.63 |

A linear Stern-Volmer slope of 0.0099 was obtained.

Importantly, an equivalent linear Stern-Volmer slope can be obtained from the demodulation factors for the excimer ($m_e$) and for the monomer ($m_m$) in accordance with the following relationship: $\tau_o/\tau=\{[(m_m/m_e)_2-1]\}^{1/2}$, where $\tau_o$ and $\tau$ are lifetimes for the excimer emission in the absence and the presence of the analyte, respectively, deconvolved from the kinetics for indirect generation of the excimer from the monomer. Further, it should be noted that the equivalent linear Stern-Volmer slope can be obtained using the intensity ratio method.

EXAMPLE 7a

This Example illustrates the preparation of bichromophoric excimer-forming compounds which can be covalently attached to a polymeric, in particular a polysiloxane, matrix material, by hydrosilation of the ketone moiety.

1,5-bis-(1-pyrene)-2,4-pentadien-3-one

To a solution of 16 g NaOH in 50 ml H₂O was added 1.0 ml tetrabutyl ammonium hydroxide titrant solution. A solution of 11.6 g 1-pyrene carboxaldehyde, 1.6 g acetone, and 50 ml $CH_2Cl_2$ was added to the basic solution; a dark orange precipitate formed immediately. The mixture was allowed to stir from 1 to 12 hours. The mixture was diluted with 100 ml H₂O and 100 ml $CH_2Cl_2$ and filtered through a glass frit. The solid was washed with $CH_2Cl_2$, ethanol, methanol, and air dried. The solid was broken up, triturated with 100 ml $CH_2Cl_2$, filtered and air dried to yield 7.20 g 1,5-bis-(1-pyrene)-2,4-pentadien-3-one, m.p 279°–281° C.

1,5-bis-(1-pyrene)-3-pentanone

Zinc dust, 22 g, was added in small batches to a solution of 3.5 g 1,5-bis-(1-pyrene)-2,4-pentadien-3-one in refluxing acetic acid. The orange color dissipated to yield a yellow solution. The solution was decanted into water and extracted with methylene chloride; the zinc was washed with $CH_2Cl_2$/water. The combined organic layers were dried over $Na_2SO_4$. Evaporation of solvent yielded 2.71 g crude product. Thin layer chromatography of 2.4 g crude product from the reduction on silica gel (Kieselgel, 70–230 mesh) using toluene as eluent produced five bands; the fourth, with $R_f$=0.25, contained the desired product by NMR. After drying, it may be used as described in Example 7b, below.

EXAMPLE 7b

This is an example of the preparation of a film containing a polymer-attached or covalently bonded intramolecular excimer component-forming moiety. To 0.05 g of polymethylhydrosiloxane (as described in Example 5) was added 0.50 ml of a $9 \times 10^{-5}$M $CH_2Cl_2$ solution of 1,5-bis-(1-pyrene)-3-pentanone, and 10 microliters of the Pt catalyst solution (as described in Example 5). This mixture was allowed to react for five minutes, then was added to 0.50 g of vinyl terminated siloxane (as described in Example 5). An additional 10 microliters of the Pt catalyst solution was added. The mixture was agitated and poured into a 57 mm diameter aluminum weighing pan and allowed to dry and curing in air, then further dried under vacuum overnight to remove residual solvent. The film thus obtained was optically clear.

This film when excited with a monochromic light, for example, at 345 nm, in the presence of varying concentrations of oxygen, provides both a monomer derived emission and a longer wavelength excimer component derived emission. Both emissions are dynamically quenchable by oxygen.

EXAMPLE 8a

This example illustrates the preparation of bichromophoric excimer-forming compounds which can be covalently attached to a polymeric, in particular a polysiloxane, matrix material, by hydrosilation of the allyl moiety.

In this example (8a) and the next example (8b), the synthesis of α-pyrenylmethyl and α-perylenylmethyl disubstituted (both symmetrical and unsymmetrical) derivatives as illustrated in Structure 1 and 2 is described.

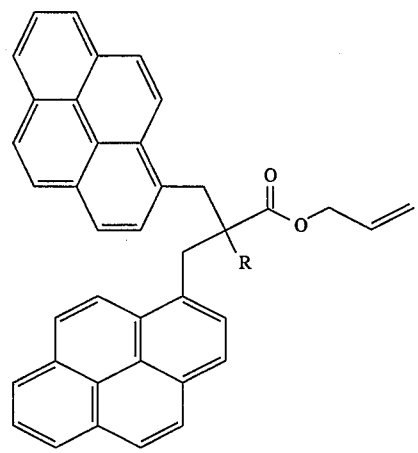

STRUCTURE 1

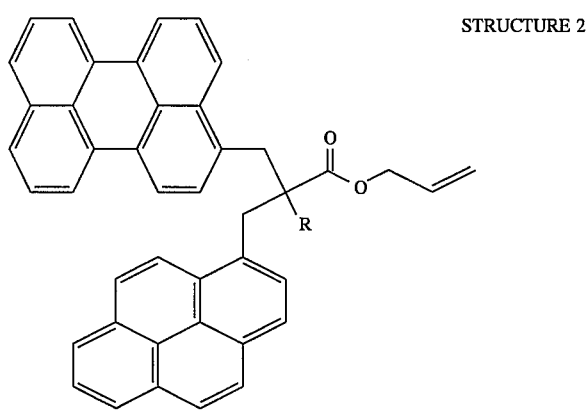

STRUCTURE 2

A general procedure for the synthesis of the compounds of Structure 1 (i.e., with the same substituents at the α-position) involves the reaction of the appropriate chloromethyl derivatives of the aromatic compounds with anions of, for example, malonates or cyanoacetates. For example, 1-chloromethylpyrene may be prepared by a two-step procedure: reduction of 1-pyrenecarboxaldehyde with sodium borohydride, followed by chlorination with thionyl chloride.

For example, the reaction of 1-chloromethylpyrene with diallyl malonate or allyl cyanoacetate may be carried out in refluxing benzene in the presence of sodium hydride to produce diallyl 2,2-bis(pyrenylmethyl)malonate (where $R=CO_2CH_2CH=CH_2$) and allyl 2-cyano-2,2-bis(pyrenylmethyl)acetate (where $R=CN$) respectively. Alternatively, R may be any acceptable group, preferably organic, which does not undesirably diminish the analyte sensitivity of the compound.

The synthesis of the unsymmetrical compounds illustrated in Structure 2 first requires the preparation of the mono-substituted derivative (e.g., as illustrated in Structure 3 or 4 where R is as described above) as an intermediate.

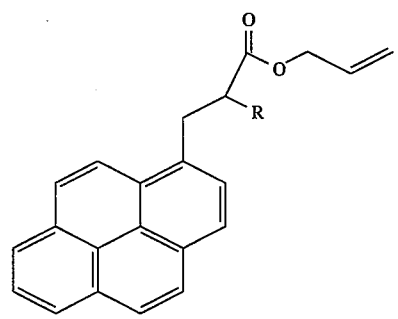

STRUCTURE 3

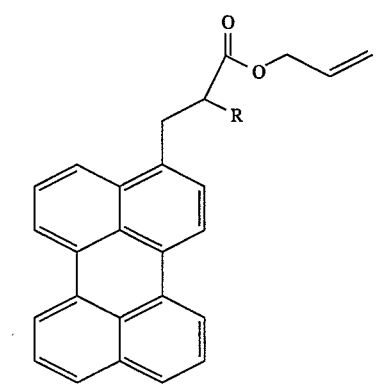

STRUCTURE 4

A suitable approach to preparing the monosubstituted derivative illustrated in Structure 3 (where $R=CO_2CH_2CH=CH_2$) is a Knoevenagel condensation of pyrenecarboxaldehyde with diallyl malonate followed by reduction of the resulting alkene derivative.

The reaction of pyrenecarboxaldehyde with diallyl malonate may be carried out in refluxing benzene with piperidinium acetate as the catalyst to produce the alkene derivative illustrated in Structure 5.

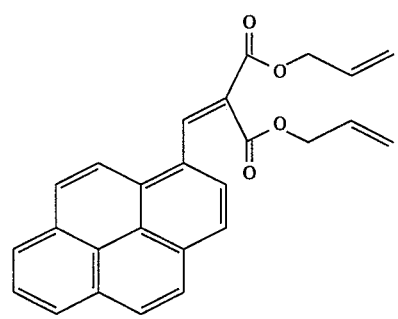

STRUCTURE 5

Nucleophilic reducing agents should preferably be employed to avoid the possible reduction of the allyl double bonds. The alkene derivative is preferably reduced using NaCNBH₃ in allyl alcohol. Allyl alcohol is used to prevent undesirable transesterification.

A Knoevenagel condensation of 3-perylenecarboxaldehyde with diallyl malonate may be employed to produce the corresponding alkene illustrated in Structure 6.

STRUCTURE 6

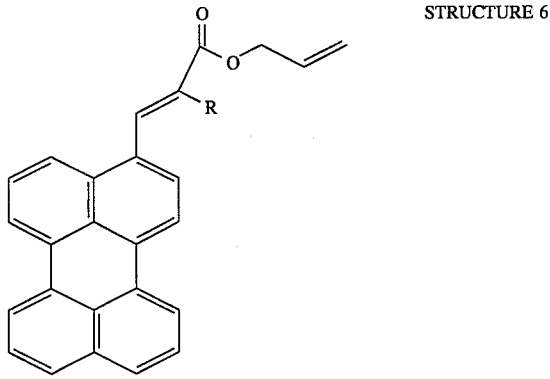

Reduction of this alkene with NaCNBH₃ in allyl alcohol may be employed to produce diallyl 2-perylenylmethylmalonate. This may then be treated with NaH in dry toluene followed by reflux with 1-chloromethylpyrene to give diallyl 2-perylenylmethyl-2-pyrenylmethylmalonate. By using the same methodology, allyl 2-cyano-2-perylenylmethyl-2-pyrenylmethylacetate may be synthesized.

1-Hydroxymethylpyrene

To a suspension of pyrene carboxaldehyde (9.6 g, 42 mmol) in ethanol (50 mL) was added NaBH₄ (2 g) and the mixture was stirred at room temperature for 6 hours. Water (100 mL) was added and the mixture was extracted with ether (2×50 mL). The organic layer was dried over MgSO₄, and the solvent evaporated under reduced pressure to give a light-yellow solid which was recrystallized from ethyl acetate to afford prisms, m.p. 125°–126° C., yield: 8.3 g, 86%.

1-Chloromethylpyrene

Thionyl chloride (15 mL, 200 mmol) was added dropwise to a suspension of 1-hydroxymethylpyrene (9.3 g, 40 mmol) in dry benzene (150 mL) at 0° C. and the mixture was stirred at room temperature overnight. Evaporation of the solvent under reduced pressure gave a creamy-white solid, m.p. 146°–148° C., yield: 9.6 g, 96%.

Diallyl 2,2-bis(pyrenylmethyl)malonate

Diallyl malonate (0.36 g, 2.0 mmol) was added to a stirred suspension of NaH (2.5 mmol) in dry benzene (5 mL). After 30 minutes 1-chloromethylpyrene (0.5 g, 2.0 mmol) in benzene (20 mL) was added. The mixture was gently refluxed for 18 hours, cooled to room temperature and washed with saturated aqueous NaCl (2×5 mL). The organic layer was dried over MgSO₄ and the solvent evaporated under reduced pressure to give the product, which was recrystallized from AcOEt/hexane to afford the desired product as white crystals, yield: 0.26 g, 42%, m.p. 178°–180° C. ¹H NMR and ¹³C NMR were in accord with the desired product. Analysis ($C_{43}H_{32}O_4$): calculated C:84.29, H:5.26; found: C:84.13, H:5.23.

A silicone film of this material could be made in a manner analogous to that used in Example 7b. With excitation at 345 nm and a concentration for the molecule of $10^{-5}$M, the monomer Stern-Volmer slope is 0.014 mm$^{-1}$, the excimer slope is 0.043 mm$^{-1}$, and the ratio slope is 0.0065 mm$^{-1}$. The monomer intensity was measured from 360–400 nm, the excimer intensity was measured from 450–600 nm. Further, it should be noted that equivalent Stern-Volmer slopes can be measured using phase modulation methods.

EXAMPLE 8b

This example further illustrates the preparation of bichromophoric excimer-forming compounds which can be covalently attached to a polymeric, in particular a polysiloxane, matrix material, by hydrosilation of the allyl moiety.

Allyl 2,2-bis(pyrenylmethyl)cyanoacetate

Allyl 2,2-bis(pyrenylmethyl)cyanoacetate was prepared by the same method as in Example 8a, using allylcyano acetate in place of diallyl malonate. Yield: 38%, m.p. 181°–183° C. ¹H NMR and ¹³C NMR were in accord with the desired product. Analysis ($C_{40}H_{27}NO_2$): calculated: C:86.78, H:4.92, N:2.53; found: C:86.51, H:4.95, N:2.46.

A silicone film of this material could be made in a manner analogous to that used in Example 7b. With excitation at 345 nm and a concentration for the molecule of $10^{-5}$M, the monomer Stern-Volmer slope is 0.007 mm$^{-1}$, the excimer slope is 0.018 mm$^{-1}$, and the ratio slope is 0.0051 mm$^{-1}$. The monomer intensity was measured from 360–400 nm, the excimer intensity was measured from 450–600 nm. Further, it should be noted that equivalent Stern-Volmer slopes can be measured using phase modulation methods.

EXAMPLE 9

This is an example of the preparation of a film containing an intramolecular exciplex component-forming moiety. To 0.50 g of a vinyl terminated siloxane (sold by Petrarch Systems Under the trademark PS441) were added 0.05 g of a polymethylhydrosiloxane (sold by Petrarch Systems under the trademark PS123), 0.50 ml of a $8 \times 10^{-4}$M $CH_2Cl_2$ solution of 1-(1-naphthyl)-2-(diethylamino)ethane, and 10 microliters of Pt catalyst solution.

The Pt catalyst solution used in these preparations was a solution of Karsted's catalyst in hexane. The solvents used were spectral grade, dried over molecular sieves. 1-(naphthyl)-2-(diethylamino) ethane was prepared according to methods outlined by Chandross and Thomas in Chem. Phys. Letters 9 393(1971). 1-napthylenyl acetic acid was converted to the acid chloride, reacted with diethylamine to make the corresponding amide and reduced to the corresponding amine using lithium aluminum hydride. Extraction from basic aqueous solution into ether gave the desired product in high yield.

The mixture was agitated and poured into a 57 mm diameter aluminum weighing pan and allowed to dry and cure in air, then further dried under vacuum overnight to remove residual solvent. The films thus obtained are optically clear.

The response of this film to oxygen was determined in the intensity mode. Upon being excited at 285 nm, exciplex emission was monitored at 420 nm and monomer emission at 308 nm. Both exciplex emission and monomer emission were dynamically quenchable by oxygen. When plotted in Stern-Volmer form there was obvious curvature of the exciplex oxygen dependence. However, the exciplex/monomer ratio in a Stern-Vomer treatment produced a linear response with a slope of 0.0025 mm$^{-1}$.

EXAMPLE 10

The response of the film produced in Example 9 is determined in phase. The film is placed in a thermostated optical isolation chamber equipped with a port for collinear excitation and emission optical fibers and ports for rapid gas exchange. The fiber optic port is positioned to provide for excitation and emission collection at an angle of 45 degrees from the film surface to minimize scatter. Emission wavelengths for exciplex emission and for monomer emission are serially selected using a standard monochrometer. The sensor film is exposed to oxygen in nitrogen mixtures with compositions ranging from 0 to 20% oxygen.

Uncorrected phase shifts is obtained from MHF or from single frequency data. These phase shifts can be referenced to the excitation source phase and included phase offsets associated with the electronics and optics.

By plotting tan $\Delta\theta_o$/tan $\Delta\theta$ vs $O_2$ concentration, a substantially linear Stern-Volmer slope is obtained. Thus, this exciplex-forming system is useful as a sensing dement in an oxygen sensor.

EXAMPLE 11

This is an example involving the use of freely diffusing donor and acceptor molecules in solution to determine the concentration of an analyte, in this case oxygen.

A solution of $7.2 \times 10^{-6}$M anthracene and 15.7 mM diethylaniline in toluene as solvent was exposed to oxygen in nitrogen mixtures containing 0, 5, 10, 15, 20% by volume oxygen. Anthracene was photoexcited at 379 nm. Monomer emission was monitored at 402 nm. Exciplex emission was monitored at 520 mn. The exciplex/monomer intensity ratio was determined at each oxygen concentration (E/M) and under nitrogen alone $(E/M)_o$. In Stern-Volmer treatment, plots of (E/M)o/(E/M) vs. oxygen concentration were linear with a slope of 0.039 $mm^{-1}$. Furthermore, this slope was invariant to variations in the concentration of diethylaniline over the range of 15.7–55.0 mM, despite the fact that the exciplex/monomer ratio itself varied substantially. This example illustrates that, while the ratio of exciplex to monomer emission intensity varies with donor concentration, conditions can be found where Stern-Volmer slopes based on the exciplex/monomer ratio are independent of donor concentration. Similar behavior can be expected for Stern-Volmer slopes based on the phase difference or demodulation factor ratio methods described in Example 10.

EXAMPLE 12

Using the sensor film and instrumentation outlined in Example 6, the phase shift difference between the excimer and monomer emissions was determined at several modulation frequencies (ringing from 1 to 50 MHz) as a function of oxygen partial pressure. These data are shown in Table 12a below.

TABLE 12a $\Delta\theta = \theta_{excimer} - \theta_{monomer}$ for $O_2$ Sensor

| | Modulation Frequency (MHz) | | | | | | |
|---|---|---|---|---|---|---|---|
| % $O_2$ | 1 | 3 | 5 | 10 | 20 | 30 | 50 |
| 0.0 | 19.1 | 46.0 | 59.9 | 74.0 | 81.8 | 84.5 | 86.7 |
| 5.09 | 14.8 | 38.4 | 52.8 | 69.3 | 79.3 | 82.8 | 85.7 |
| 10.35 | 11.7 | 31.9 | 46.0 | 64.3 | 76.4 | 80.9 | 84.5 |
| 15.37 | 10.0 | 27.8 | 41.3 | 60.7 | 74.1 | 79.3 | 83.5 |

By interpolation, modulation frequencies were calculated which will provide a constant phase shift of 45 degrees at each oxygen concentration. Table 12b illustrates the linear relationship between modulation frequency and analyte concentration at constant phase shift (i.e., phase-modulation mode 3).

TABLE 12b

| % $O_2$ | Frequency @ $\Delta\theta = 45°$ (MHz) |
|---|---|
| 0.00 | 2.926 |
| 5.09 | 3.917 |
| 10.35 | 4.858 |
| 15.37 | 5.954 |

Based on the calibration relationship derived for an individual excimer emission characterized by an impulse response function with lifetime $\tau_o$, $f=((\tan\theta)/2\pi)[1/\tau_o + ak_q P_{O2}]$, where a=solubility of oxygen in the silicone matrix and $k_q$=bimolecular quenching rate constant for collisional quenching of the excimer by oxygen.

While this invention has been described with respect to various specific examples and embodiments, it is to be understood that the invention is not limited thereto and that it can be variously practiced within the scope of the following claims.

What is claimed is:

1. A method for sensing the concentration of an analyte in a medium comprising the steps of:

exposing a sensing element to said medium, said sensing element comprising an analyte permeable matrix material and an indicator component in said matrix material comprising at least two monomeric components in enforced association, at least one of which is a monomeric indicator component which provides a first emitted signal or signals in response to being exposed to a first excitation signal, said sensing element further comprising, when exposed to said first excitation signal, an excited state complex produced from said at least two monomeric components, said excited state complex providing a second emitted signal which is dependent on the concentration of said analyte in said medium;

causing said sensing element to provide said first emitted signal or signals and said second emitted signal; and analyzing said second emitted signal in determining the concentration of said analyte in said medium.

2. The method of claim 1, wherein said analyzing step includes determining an intensity ratio of said second emitted signal to said first emitted signal or at least one of said first emitted signals, said intensity ratio being dependent on the concentration of said analyte in said medium.

3. The method of claim 1, wherein said first emitted signal or at least one of said first emitted signals and said second emitted signal are modulated, and at least one of: an extent of a phase shift between a modulated second excitation signal and said modulated second emitted signal; or an extent of a phase shift between said modulated first emitted signal or at least one of said modulated first emitted signals and said modulated second emitted signal; or an extent of a phase shift between a combined modulated first and second emitted signals and said first excitation signal or signals; or a magnitude of relative demodulation between said modulated second excitation signal and said modulated second emitted signal; or a ratio of demodulation factors of said modulated first emitted signal or at least one of said modulated first emitted signals and said modulated second emitted signal; or a magnitude of relative demodulation between a combined modulated first emitted signal or signals and the modulated second emitted signal; or a excitation frequency necessary to maintain a fixed phase shift between said modulated first and second emitted signals is dependent on the concentration of said analyte in said medium and wherein a processor assembly is adapted to determine at least one of said phase shift, said demodulation factor, or said excitation frequency.

4. A method for sensing the concentration of an analyte in a medium comprising the steps of:

exposing a sensing element to said medium, said sensing element comprising an analyte permeable matrix material and at least two different monomeric components at least one of which is a monomeric indicator component which provides a first emitted signal or signals in response to being exposed to a first excitation signal, said sensing element further comprising, when exposed to said first excitation signal, an exciplex component produced from said at least two monomeric components, said exciplex component providing a second emitted signal which is dependent on the concentration of said analyte in said medium wherein at least one of said monomeric components is covalently bonded to said matrix material;

causing said sensing element to provide said first emitted signal or signals and said second emitted signal; and analyzing said first emitted signal or signals and said second emitted signal in determining the concentration of said analyte in said medium.

5. The method of claim 4, wherein said analyzing step includes determining an intensity ratio of said second emitted signal to said first emitted signal or at least one of said first emitted signals, said intensity ratio being dependent on the concentration of said analyte in said medium.

6. The method of claim 4, wherein said first emitted signal or at least one of said first emitted signals and said second emitted signal are modulated, and at least one of: an extent of a phase shift between a modulated second excitation signal and said modulated second emitted signal; or an extent of a phase shift between said modulated first emitted signal or at least one of said modulated first emitted signals and said modulated second emitted signal; or an extent of a phase shift between a combined modulated first and second emitted signals and said first excitation signal or signals; or a magnitude of relative demodulation between said modulated second excitation signal and said modulated second emitted signal; or a ratio of demodulation factors of said modulated first emitted signal or at least one of said modulated first emitted signals and said modulated second emitted signal; or a magnitude of relative demodulation between a combined modulated first emitted signal or signals and the modulated second emitted signal; or an excitation frequency necessary to maintain a fixed phase shift between said modulated first and second emitted signals is dependent on the concentration of said analyte in said medium and wherein a processor assembly is adapted to determine at least one of said phase shift, said demodulation factor, or said excitation frequency.

7. A method for sensing the concentration of an analyte in a medium comprising the steps of:

exposing a sensing element to said medium, said sensing element comprising an analyte permeable matrix material and .at least two different monomeric components at least one of which is a monomeric indicator component which provides a first emitted signal or signals in response to being exposed to a first excitation signal, said sensing element further comprising, when exposed to said first excitation signal, an exciplex component produced from said at least two monomeric components, said exciplex component providing a second emitted signal which is dependent on the concentration of said analyte in said medium, and wherein a total integrated intensity at the wavelength of the second emitted signal has less than ten percent contribution due to monomer emission;

causing said sensing element to provide said first emitted signal or signals and said second emitted signal; and analyzing said first emitted signal or signals and said second emitted signal in determining the concentration of said analyte in said medium.

8. The method of claim 7, wherein said analyzing step includes determining an intensity ratio of said second emitted signal to said first emitted signal or at least one of said first emitted signals, said intensity ratio being dependent on the concentration of said analyte in said medium.

9. The method of claim 7, wherein said first emitted signal or at least one of said first emitted signals and said second emitted signal are modulated, and at least one of: an extent of a phase shift between a modulated second excitation signal and said modulated second emitted signal; or an extent of a phase shift between said modulated first emitted signal or at least one of said modulated first emitted signals and said modulated second emitted signal; or an extent of a phase shift between a combined modulated first and second emitted signals and said first excitation signal or signals; or a magnitude of relative demodulation between said modulated second excitation signal and said modulated second emitted signal; or a ratio of demodulation factors of said modulated first emitted signal or at least one of said modulated first emitted signals and said modulated second emitted signal; or a magnitude of relative demodulation between a combined modulated first emitted signal or signals and the modulated second emitted signal; or an excitation frequency necessary to maintain a fixed phase shift between said modulated first and second emitted signals is dependent on the concentration of said analyte in said medium and wherein a processor assembly is adapted to determine at least one of said phase shift, said demodulation factor, or said excitation frequency.

10. A method for sensing the concentration of an analyte in a medium comprising the steps of:

exposing a sensing element to said medium, said sensing element comprising an analyte permeable matrix material and at least two monomeric components at least one of which is a monomeric indicator component which provides a first emitted signal or signals in response to being exposed to a first excitation signal, said sensing element further comprising, when exposed to said first excitation signal, an excited state complex produced from said at least two monomeric components, said excited state complex providing a second emitted signal having a longer wavelength than said first emitted signal and being dependent on the concentration of said analyte in said medium wherein at least one of said monomeric components is covalently bonded to said matrix material;

causing said sensing element to provide said first emitted signal or signals and said second emitted signal; and analyzing said first emitted signal or signals and said second emitted signal in determining the concentration of said analyte in said medium.

11. The method of claim 10, wherein said analyzing step includes determining an intensity ratio of said second emitted signal to said first emitted signal or at least one of said first emitted signals, said intensity ratio being dependent on the concentration of said analyte in said medium.

12. The method of claim 10, wherein said first emitted signal or at least one of said first emitted signals and said second emitted signal are modulated, and at least one of: an extent of a phase shift between a modulated second excitation signal and said modulated second emitted signal; or an extent of a phase shift between said modulated first emitted signal or at least one of said modulated first emitted signals and said modulated second emitted signal; or an extent of a phase shift between a combined modulated first and second emitted signals and said first excitation signal or signals; or a magnitude of relative demodulation between said modulated second excitation signal and said modulated second emitted signal; or a ratio of demodulation factors of said modulated first emitted signal or at least one of said modulated first emitted signals and said modulated second emitted signal; or a magnitude of relative demodulation between a combined modulated first emitted signal or signals and the modulated second emitted signal; or an excitation frequency necessary to maintain a fixed phase shift between said modulated first and second emitted signals is dependent on the concentration of said analyte in said medium and wherein a processor assembly is adapted to determine at least one of said phase shift, said demodulation factor, or said excitation frequency.

13. A method for sensing the concentration of an analyte in a medium comprising the steps of:

exposing a sensing element to said medium, said sensing element comprising at least two monomeric components, at least one of which is a monomeric indicator component which provides a first emitted signal or signals in response to being exposed to a first excitation signal, said sensing element further comprising, when exposed to said first excitation signal, an excited state complex produced from said at least two monomeric components, said excited state complex providing a second emitted signal;

causing said sensing element to provide said first emitted signal or signals and said second emitted signal; and analyzing said first emitted signal or signals and said second emitted signal in determining the concentration of said analyte in said medium, wherein said first emitted signal or at least one of said first emitted signals and said second emitted signal are modulated, and at least one of: an extent of a phase shift between a modulated second excitation signal and said modulated second emitted signal; or an extent of a phase shift between said modulated first emitted signal or at least one of said modulated first emitted signals and said modulated second emitted signal; or an extent of a phase shift between a combined modulated first and second emitted signals and said first excitation signal or signals; or a magnitude of relative demodulation between said modulated second excitation signal and said modulated second emitted signal; or a ratio of demodulation factors of said modulated first emitted signal or at least one of said modulated first emitted signals and said modulated second emitted signal; or a magnitude of relative demodulation between a combined modulated first emitted signal or signals and the modulated second emitted signal; or an excitation frequency necessary to maintain a fixed phase shift between said modulated first and second emitted signals is dependent on the concentration of said analyte in said medium and wherein a processor assembly is adapted to determine at least one of said phase shift, said demodulation factor, or said excitation frequency.

14. The method of claim 13, wherein said monomeric components are covalently bonded together.

15. The method of claim 1, wherein said at least two monomeric components are covalently bonded together.

16. The method of claim 1, wherein said at least two monomeric components are different and said produced excited state complex is an exciplex component.

17. The method of claim 1, wherein said indicator component is covalently bonded to said solid matrix material.

18. The method of claim 1, wherein said monomeric components in enforced association are selected from the group consisting of intramolecular excited state complex forming molecules dispersed in a matrix material, intramolecular excited state complex forming molecules covalently attached, adsorbed or otherwise attached to the surface of a matrix material, intramolecular excited state complex forming molecules covalently attached to a matrix material, monomeric component aggregates covalently attached to a matrix material, monomeric component aggregates adsorbed to the surface of a matrix material, an inclusion complex comprising a supra-molecule, and ionically bound monomeric components.

19. The method of claim 4, wherein at least two of said monomeric components are covalently bonded to said matrix material.

20. The method of claim 4, wherein said at least two different monomeric components are covalently bonded together.

21. The method of claim 7, wherein said at least two different monomeric components are linked by less than 20 atoms.

22. The method of claim 10, wherein said at least two monomeric components are covalently bonded together or to said matrix material.

23. The method of claim 10, wherein said at least two monomeric components are different and said produced excited state complex is an exciplex component.

24. The method of claim 13, wherein said at least two monomeric components are covalently bonded together.

25. The method of claim 13, wherein said at least two monomeric components are different and said produced excited state complex is an exciplex component.

26. The method of claim 1, wherein said analyte comprises oxygen, said medium comprises blood, and said matrix comprises a silicone material.

27. The method of claim 1, wherein said indicator component comprises a polynuclear aromatic compound.

28. The method of claim 1, wherein said indicator component comprises a polynuclear aromatic compound selected from the group consisting of perylene, decacyclene, benzoperylene, coronene, pyrene, porphycine, porphyrin, chlorin, phthalocyanine and derivatives and mixtures thereof.

29. The method of claim 7, wherein said exciplex component comprises at least one polynuclear aromatic monomeric component selected from the group consisting of biphenyl, naphthalene, phenanthrene, p-terphenyl, chrysene, benzpyrene, pyrene, dibenzanthrene, benzanthrene, anthracene, perylene, benzperylene, fluoranthene, coronene, quinoline, phenylquinoline, benzquinoline, quinoxaline, dibenzquinoxaline, benzquinoxaline, phthalimide, pyridine, phenazine, dibenzphenzine, acridine, benzacridine and derivatives of these compounds and at least one monomeric component selected from the group consisting of tetramethyl-p-phenylenediamine, dimethoxydimethylaniline, methoxydimethylaniline, diethylaniline, diphenylmethylamine, triethylamine, indole, dimethyltoluidine, tri-p-anisylamine, ditolylmethylamine, tritolylamine, triphenylamine, ethylcarbazole, trimethoxybenzene, tetramethoxybenzene and derivatives of these compounds.

30. The method of claim 7, wherein said exciplex component comprises at least one polynuclear aromatic monomeric component and at least one aliphatic or aromatic amine-containing or aromatic ether-containing monomeric component.

31. The method of claim 7, wherein said exciplex component comprises at least one aromatic nitrite monomeric component and at least one monomeric component selected from the group consisting of polynuclear aromatic monomeric components, aliphatic or aromatic amine-containing or aromatic ether-containing monomeric components.

* * * * *

UNITED STATES PATENT AND TRADEMARK OFFICE
CERTIFICATE OF CORRECTION

PATENT NO.: 5,498,549

DATED: March 12, 1996

INVENTOR(S): Colleen C. Nagel, James G. Bentsen, Masao Yafuso, Alan R. Katritzky, John L. Dektar and Cary A. Kipke It is certified that error appears in the above-identified patent and that said Letters Patent is hereby corrected as shown below:

Col. 2, line 31, "Barnet" should read -- Barner --.

Col. 16, line 39, "Co)" should read -- (b) --.

Col. 16, line 51, "Stem" should read -- Stern --.

Col. 18, line 55, "polyallcy-" should read -- polyalkyl--

Col. 20, line 39, "moleties" should read -- moieties --.

Col. 21, line 29, "moleties" should read -- moieties --.

Col. 26, line 19, "moleties" should read -- moieties --.

Col. 26, line 46, "carded" should read -- carried --.

Col. 29, line 46, "Volm" should read -- Volmer --.

Col. 30, line 22, "$\tau_0/\tau=\{[(m_m/m_e)_2-1]\}^{1/2}$" should read -- $\tau_0/\tau=\{[(m_m/m_e)_0^2-1]/[(m_m/m_e)^2-1]\}^{1/2}$ --.

Col. 35, line 49, "ringing" should read -- ranging --.

Col. 18, line 56, delete "$\ell$" before "(aryl)".

Signed and Sealed this

Fifth Day of May, 1998

BRUCE LEHMAN

*Attest:*

*Attesting Officer*    Commissioner of Patents and Trademarks